(12) United States Patent
Kleemann

(10) Patent No.: US 7,772,262 B2
(45) Date of Patent: Aug. 10, 2010

(54) SUBSTITUTED BENZOYLGUANIDINES, METHOD FOR PRODUCTION AND USE THEREOF AS MEDICAMENT OR DIAGNOSTIC AND MEDICAMENT COMPRISING THE SAME

(75) Inventor: Heinz-Werner Kleemann, Bischofsheim (DE)

(73) Assignee: sanofi-aventis Deutschland GmbH, Frankfurt am Main (DE)

( * ) Notice: Subject to any disclaimer, the term of this patent is extended or adjusted under 35 U.S.C. 154(b) by 34 days.

(21) Appl. No.: 11/748,166

(22) Filed: May 14, 2007

(65) Prior Publication Data

US 2007/0270414 A1 Nov. 22, 2007

Related U.S. Application Data

(63) Continuation of application No. PCT/EP2005/011595, filed on Oct. 29, 2005.

(30) Foreign Application Priority Data

Nov. 13, 2004 (DE) .................. 10 2004 054 847

(51) Int. Cl.
    *C07D 285/16* (2006.01)
    *C07D 275/02* (2006.01)
    *A61K 31/54* (2006.01)
(52) U.S. Cl. ...................... 514/372; 548/214
(58) Field of Classification Search ............. 548/214; 514/372

See application file for complete search history.

(56) References Cited

FOREIGN PATENT DOCUMENTS

| WO | WO00/30624 | 6/2000 |
|---|---|---|
| WO | WO 03/106410 | 12/2003 |
| WO | WO2005/082895 | 9/2005 |

OTHER PUBLICATIONS

Chalmers (TiPS vol. 17, pp. 166-172 Apr. 1996).*
Zeid et al. Justus Liebigs Annalen der Chemie (1974), (4), 667-70.*
Baumgarth, M. et al., Bicyclic Acylguanidine Na+/H+ Antiporter Inhibitors, J. Med. Chem. (1998), 41, 3736-3747.
Baumgarth, M. et al., (2-Methyl-5-(methylsulfonyl)benzoyl) guanidine Na+/H+ Antiporter Inhibitors, Journal of Medicinal Chemistry, 1997, vol. 40. No. 13, 2017-2034.
Karmazyn, M., Inhibitors of Sodium-Hydrogen Exchange as Therapeutic Agents for the Treatments of Heart Disease, Expert Opin. Ther. Patents (2003) 13(9) 1411-1425.
Weichert, A. et al., Synthesis of the Highly Selective Na+/H+ Exchange Inhibitors Cariporide Mesilate and (3-Methanesulfonyl-4-piperidino-benzoyl) guanidine Methanesulfonate, Arzneim-Forsch/Drug Res. 47 (II), Nr. 11 (1997) 1204-1207.

* cited by examiner

*Primary Examiner*—Kahsay T Habte
(74) *Attorney, Agent, or Firm*—James W. Bolcsak

(57) ABSTRACT

The present invention relates to substituted benzoylguanidines of the formula I:

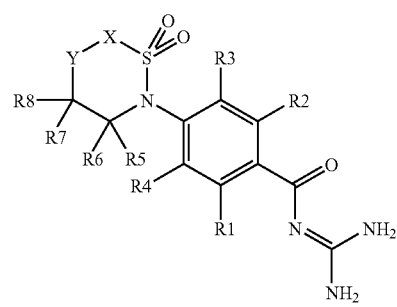

I in which R1 to R8 and X and Y are as described in the specification, and their pharmaceutically acceptable salts are substituted acylguanidines as inhibitors of the cellular sodium-proton antiporter ($Na^+/H^+$ exchanger, NHE).

7 Claims, 1 Drawing Sheet

SUBSTITUTED BENZOYLGUANIDINES, METHOD FOR PRODUCTION AND USE THEREOF AS MEDICAMENT OR DIAGNOSTIC AND MEDICAMENT COMPRISING THE SAME

CROSS REFERENCE TO RELATED APPLICATIONS

This application is a continuation of International Application No. PCT/EP2005/011595 filed on Oct. 29, 2005, which is hereby incorporated by reference, which claims the benefit of priority from German Application: DE 10 2004 054847.1, filed on Nov. 13, 2004, which is hereby incorporated by reference.

DETAILED DESCRIPTION OF THE INVENTION

Substituted benzoylguanidines of the formula I

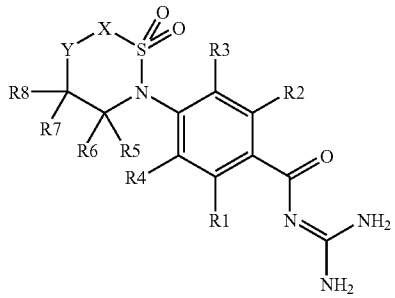

Figure 1:
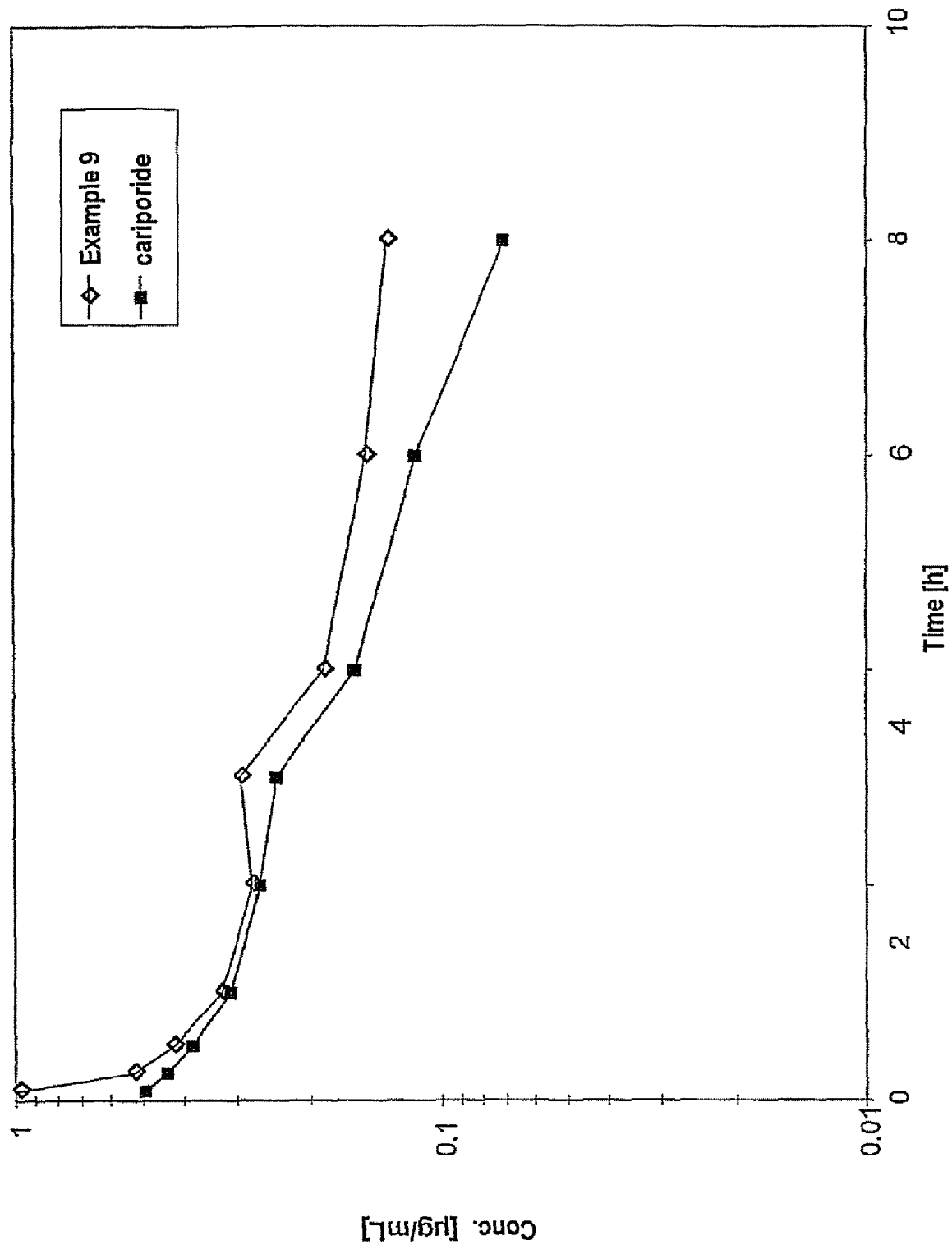
FIG. 1: shows concentration-time plots in the blood plasma of dogs after administration of, in each case, approximately 1 mg/kg of the compound of Example 9 and of cariporide.
y axis: concentration of the measured compound in the μg/ml in plasma
x axis: time in h

in which R1 to R8 and X and Y have the meanings indicated below, and their pharmaceutically acceptable salts are substituted acylguanidines and inhibit the cellular sodium-proton antiporter ($Na^+/H^+$ exchanger, NHE). Because of the NHE-inhibitory properties, the compounds of the formula I and their pharmaceutically acceptable salts are suitable for the prevention and treatment of diseases caused by activation or by an activated NHE, and of diseases caused secondarily by the NHE-related damage.

Compared with known compounds, the compounds of the invention are distinguished by an extremely high activity in the inhibition of $Na^+/H^+$ exchange, and by improved ADMET properties. The structure according to the invention has an advantageous influence on tissue distribution. This leads inter alia to increased exposures in vivo. This involves no significant influence on the absorption characteristics, and the high bioavailability of the acylguanidines is retained.

In contrast to some acylguanidines described in the literature, the compounds of the formula I described herein and their pharmaceutically acceptable salts show no unwanted and disadvantageous saliduretic properties.

The invention relates to substituted benzoylguanidines of the formula I

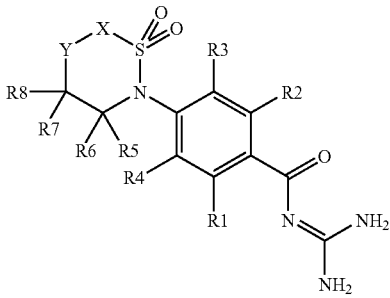

in which the meanings are
R1 hydrogen, alkyl having 1, 2, 3 or 4 carbon atoms, alkoxy having 1, 2, 3 or 4 carbon atoms, F, Cl, Br, I, —CN, NR13R14, —O—$(CH_2)_n$—$(CF_2)_o$—$CF_3$ or —$(SO_m)_q$—$(CH_2)_r$$(CF_2)_s$—$CF_3$;
R13 and R14
independently of one another hydrogen, alkyl having 1, 2, 3 or 4 carbon atoms or —$CH_2$—$CF_3$;
m zero, 1 or 2
n, o, q, r and s
independently of one another zero or 1;
R2 hydrogen, alkyl having 1, 2, 3 or 4 carbon atoms, alkoxy having 1, 2, 3 or 4 carbon atoms, F, Cl, Br, I, —CN, NR15R16, —O—$(CH_2)_u$—$(CF_2)_v$—$CF_3$ or —$(SO_w)_x$—$(CH_2)_y$—$(CF_2)_z$—$CF_3$;
R15 and R16
independently of one another hydrogen, alkyl having 1, 2, 3 or 4 carbon atoms or —$CH_2$—$CF_3$;
w zero, 1 or 2
u, v, x, y and z
independently of one another zero or 1;
R3 hydrogen, F, Cl, Br, I, —CN, —$SO_2CH_3$, alkoxy having 1, 2, 3 or 4 carbon atoms, NR9R10, —O—$(CH_2)_b$—$(CF_2)_c$—$CF_3$, —$(SO_d)_e$—$(CH_2)_f$—$(CF_2)_g$—$CF_3$, alkyl having 1, 2, 3, 4, 5 or 6 carbon atoms or cycloalkyl having 3, 4, 5, 6, 7 or 8 carbon atoms, in which 1, 2, 3 or 4 hydrogen atoms may be replaced by fluorine atoms;
R9 and R10
independently of one another hydrogen, alkyl having 1, 2, 3 or 4 carbon atoms or —$CH_2$—$CF_3$;
b, c, e and g
independently of one another zero or 1;
d zero, 1 or 2;
f zero, 1, 2, 3 or 4;
or
R3 —$(CH_2)_h$-phenyl or —O-phenyl, in which the phenyl radicals are unsubstituted or are substituted by 1, 2 or 3 radicals selected from the group consisting of series F, Cl, Br, I, —$O_j$—$(CH_2)_k$—$CF_3$, alkoxy having 1, 2, 3 or 4 carbon atoms, alkyl having 1, 2, 3 or 4 carbon atoms and —$SO_2CH_3$;
j zero or 1;
k zero, 1, 2 or 3;
h zero, 1, 2, 3 or 4;
or
R3 —$(CH_2)_{aa}$-heteroaryl,
which is unsubstituted or is substituted by 1, 2 or 3 radicals selected from the group consisting of F, Cl, Br, I, —$O_{bb}$—$(CH_2)_{cc}$—$CF_3$, alkoxy having 1, 2, 3 or 4 carbon atoms, alkyl having 1, 2, 3 or 4 carbon atoms and —SO$_2$CH$_3$;
bb zero or 1;
cc zero or 1, 2 or 3;
aa zero, 1, 2, 3 or 4;
R4 hydrogen, F, Cl, Br, I, —CN, —SO$_2$CH$_3$, alkoxy having 1, 2, 3 or 4 carbon atoms, NR11R12, —O—(CH$_2$)$_{ee}$—(CF$_2$)$_{ff}$—CF$_3$; —(SO$_{gg}$)$_{hh}$—(CH$_2$)$_{jj}$—(CF$_2$)$_{kk}$—CF$_3$, alkyl having 1, 2, 3, 4, 5 or 6 carbon atoms or cycloalkyl having 3, 4, 5, 6, 7 or 8 carbon atoms, in which 1, 2, 3 or 4 hydrogen atoms may be substituted by fluorine atoms;
R11 and R12
independently of one another hydrogen, alkyl having 1, 2, 3 or 4 carbon atoms or —CH$_2$—CF$_3$;
ee, ff, hh and kk
independently of one another zero or 1;
gg zero, 1 or 2;
jj zero, 1, 2, 3 or 4;
or
R4 —(CH$_2$)$_{ll}$-phenyl or —O-phenyl,
in which the phenyl radicals are unsubstituted or are substituted by 1, 2 or 3 radicals selected from the group consisting of F, Cl, Br, I, —O$_{mm}$—(CH$_2$)$_{nn}$—CF$_3$, alkoxy having 1, 2, 3 or 4 carbon atoms, alkyl having 1, 2, 3 or 4 carbon atoms and —SO$_2$CH$_3$;
mm zero or 1;
nn zero, 1, 2 or 3;
ll zero, 1, 2 or 4;
or
R4 —(CH$_2$)$_{oo}$-heteroaryl,
which is unsubstituted or is substituted by 1, 2 or 3 radicals selected from the group consisting of F, Cl, Br, I, —O$_{pp}$—(CH$_2$)$_{rr}$—CF$_3$, alkoxy having 1, 2, 3 or 4 carbon atoms, alkyl having 1, 2, 3 or 4 carbon atoms and —SO$_2$CH$_3$;
pp zero or 1;
rr zero, 1, 2 or 3;
oo zero, 1, 2, 3 or 4;
R5 and R6
independently of one another hydrogen or alkyl having 1, 2, 3 or 4 carbon atoms;
R7 and R8
independently of one another hydrogen, alkyl having 1, 2, 3 or 4 carbon atoms, cycloalkyl having 3, 4, 5, 6, 7 or 8 carbon atoms, —CF$_3$ or phenyl, where the phenyl radical is unsubstituted or is substituted by 1, 2 or 3 radicals selected from the group consisting of series F, Cl, Br, I, —O$_{ss}$—(CH$_2$)$_t$—CF$_3$, alkoxy having 1, 2, 3 or 4 carbon atoms, alkyl having 1, 2, 3 or 4 carbon atoms and —SO$_2$CH$_3$;
ss zero or 1
tt zero, 1, 2 or 3;
or
R7 and R8
form together with the carbon atom carrying them a cycloalkyl having 3, 4, 5, 6, 7 or 8 carbon atoms;
X —CH$_2$— or —NR17-
R17 hydrogen, alkyl having 1, 2, 3 or 4 carbon atoms, cycloalkyl having 3, 4, 5, 6, 7 or 8 carbon atoms, —CH$_2$—CF$_3$ or phenyl which is unsubstituted or is substituted by 1, 2 or 3 radicals selected from the group consisting of F, Cl, Br, I, —O$_{uu}$—(CH$_2$)$_w$—CF$_3$, alkoxy having 1, 2, 3 or 4 carbon atoms, alkyl having 1, 2, 3 or 4 carbon atoms and —SO$_2$CH$_3$;
uu zero or 1;
w zero, 1, 2 or 3;

Y a bond or an alkylene chain having 1, 2 or 3 carbon atoms; and the pharmaceutically acceptable salts thereof.
Preference is given to compounds of the formula I in which the meanings are:
R1 hydrogen, alkyl having 1, 2, 3 or 4 carbon atoms, alkoxy having 1, 2, 3 or 4 carbon atoms, F, Cl, NR13R14, —O—(CH$_2$)$_n$—(CF$_2$)$_o$—CF$_3$ or —(SO$_m$)$_q$—(CH$_2$)$_r$—(CF$_2$)$_s$—CF$_3$;
R13 and R14
independently of one another hydrogen, methyl, ethyl or CH$_2$—CF$_3$;
m zero, 1 or 2
n, o, q, r and s
independently of one another zero or 1;
R2 hydrogen, methyl, methoxy, F, Cl, —O—CF$_3$, —O—CH$_2$—CF$_3$ or —S—CF$_3$;
R3 hydrogen, F, Cl, —CN, —SO$_2$CH$_3$, methoxy, ethoxy, NR9R10, —O—CF$_3$, —O—CH$_2$—CF$_3$, —SO$_2$CF$_3$, —S—CF$_3$, —CF$_3$, alkyl having 1, 2, 3 or 4 carbon atoms or cycloalkyl having 3, 4, 5 or 6 carbon atoms, in which 1, 2, 3 or 4 hydrogen atoms may be substituted by fluorine atoms;
R9 and R10
independently of one another hydrogen, methyl, ethyl or —CH$_2$—CF$_3$;
or
R3 phenyl or —O-phenyl,
in which the phenyl radicals are unsubstituted or are substituted by 1, 2 or 3 radicals selected from the group consisting of series F, Cl, —O—CF$_3$, —O—CH$_2$—CF$_3$, —S—CF$_3$, methoxy, ethoxy, alkyl having 1, 2, 3 or 4 carbon atoms and —SO$_2$CH$_3$;
R4 hydrogen, F, Cl, —CN, —SO$_2$CH$_3$ or methyl;
R5 and R6
independently of one another hydrogen, methyl or ethyl;
R7 and R8
independently of one another hydrogen, alkyl having 1, 2, 3 or 4 carbon atoms, cycloalkyl having 3, 4, 5 or 6 carbon atoms, —CF$_3$ or phenyl, where the phenyl radical is unsubstituted or is substituted by 1, 2 or 3 radicals selected from the group consisting of series F, Cl, —O—CF$_3$, —O—CH$_2$—CF$_3$, —S—CF$_3$, methoxy, ethoxy, alkyl having 1, 2, 3 or 4 carbon atoms and —SO$_2$CH$_3$;
or
R7 and R8
form together with the carbon atom carrying them a cycloalkyl having 3, 4, 5 or 6 carbon atoms;
X —CH$_2$— or —NR17-
R17 hydrogen, methyl, ethyl, cycloalkyl having 3, 4, 5 or 6 carbon atoms, —CH$_2$—CF$_3$ or phenyl which is unsubstituted or is substituted by 1, 2 or 3 radicals selected from the group consisting of F, Cl, Br, I, —O—CF$_3$, —O—CH$_2$—CF$_3$, —S—CF$_3$, methoxy, ethoxy, alkyl having 1, 2, 3 or 4 carbon atoms and —SO$_2$CH$_3$;
Y a bond or —CH$_2$—;
and the pharmaceutically acceptable salts thereof.
Particular preference is given to compounds of the formula I in which the meanings are:
R1 hydrogen, methyl, ethyl, methoxy, ethoxy, F, Cl, —O—CF$_3$, —O—CH$_2$—CF$_3$ or —S—CF$_3$;
R2 hydrogen, F, Cl, —O—CF$_3$, —O—CH$_2$—CF$_3$ or —S—CF$_3$;
R3 F, Cl, —CN, —SO$_2$CH$_3$, —CF$_3$, —O—CF$_3$, —O—CH$_2$—CF$_3$, —SO$_2$CF$_3$, —S—CF$_3$, alkyl having 1, 2, 3 or 4 carbon atoms or cycloalkyl having 3, 4, 5 or 6 carbon atoms, in which 1, 2, 3 or 4 hydrogen atoms may be replaced by fluorine atoms;

or
R3 phenyl or —O-phenyl, in which the phenyl radicals are unsubstituted or are substituted by 1 or 2 radicals selected from the group consisting of series F, Cl, —O—CF$_3$, —O—CH$_2$—CF$_3$, —S—CF$_3$, methoxy, ethoxy, alkyl having 1, 2, 3 or 4 carbon atoms and —SO$_2$CH$_3$;
R4 hydrogen or F;
R5 and R6
  independently of one another hydrogen or methyl;
R7 and R8
  independently of one another hydrogen, alkyl having 1, 2, 3 or 4 carbon atoms, cycloalkyl having 3, 4, 5 or 6 carbon atoms, —CF$_3$ or phenyl, where the phenyl radical is unsubstituted or is substituted by 1 or 2 radicals selected from the group consisting of series F, Cl, —O—CF$_3$, —O—CH$_2$—CF$_3$, —S—CF$_3$, methoxy, ethoxy, alkyl having 1, 2, 3 or 4 carbon atoms and —SO$_2$CH$_3$;
or
R7 and R8
  form together with the carbon atom carrying them a cycloalkyl having 3, 4, 5 or 6 carbon atoms;
X —CH$_2$— or —NR17-
  R17 hydrogen, methyl, ethyl, cycloalkyl having 3, 4, 5 or 6 carbon atoms, —CH$_2$—CF$_3$ or phenyl which is unsubstituted or substituted by 1, 2 or 3 radicals selected from the group consisting of F, Cl, Br, I, —O—CF$_3$, —O—CH$_2$—CF$_3$, —S—CF$_3$, methoxy, ethoxy, alkyl having 1, 2, 3 or 4 carbon atoms and —SO$_2$CH$_3$;
Y a bond or —CH$_2$—;
and the pharmaceutically acceptable salts thereof.

Very particular preference is given to compounds of the formula I in which the meanings are:
R1 hydrogen, methyl, —O—CH$_2$—CF$_3$ or —S—CF$_3$;
R2 hydrogen;
R3 —CN, —SO$_2$CH$_3$, —CF$_3$, —O—CF$_3$, —O—CH$_2$—CF$_3$, —SO$_2$CF$_3$, —S—CF$_3$;
R4 hydrogen;
R5 and R6
  hydrogen;
R7 hydrogen;
R8 alkyl having 1, 2, 3 or 4 carbon atoms, cycloalkyl having 3, 4, 5 or 6 carbon atoms, CF$_3$ or phenyl, where the phenyl radical is unsubstituted or is substituted by 1 or 2 radicals selected from the group consisting of series F, Cl, —O—CF$_3$, —O—CH$_2$—CF$_3$, —S—CF$_3$, methoxy, ethoxy, alkyl having 1, 2, 3 or 4 carbon atoms and —SO$_2$CH$_3$;
X —CH$_2$—
Y a bond or —CH$_2$—;
and the pharmaceutically acceptable salts thereof.

Very particular preference is likewise given to compounds of the formula I in which the meanings are:
R1 hydrogen, methyl, —O—CH$_2$—CF$_3$ or —S—CF$_3$;
R2 hydrogen;
R3 —CN, —SO$_2$CH$_3$, —CF$_3$, —O—CF$_3$, —O—CH$_2$—CF$_3$, —SO$_2$CF$_3$, —S—CF$_3$;
R4 hydrogen;
R5 and R6
  independently of one another hydrogen or methyl;
R7 hydrogen;
R8 hydrogen;
X —CH$_2$— or —NR17-
  R17 hydrogen, methyl, ethyl, cycloalkyl having 3, 4, 5 or 6 carbon atoms or —CH$_2$—CF$_3$;
Y a bond or —CH$_2$—;
and the pharmaceutically acceptable salts thereof.

In one embodiment, preference is given to compounds of the formula I in which R1 is described by hydrogen, alkyl having 1, 2, 3 or 4 carbon atoms, alkoxy having 1, 2, 3 or 4 carbon atoms, F, Cl, NR13R14, —O—(CH$_2$)$_n$—(CF$_2$)$_o$—CF$_3$ or —(SO$_m$)$_q$—(CH$_2$)$_r$—(CF$_2$)$_s$—CF$_3$, where R13 and R14 are independently of one another hydrogen, methyl, ethyl or —CH$_2$—CF$_3$, m is zero, 1 or 2, and n, o, q, r and s are independently of one another zero or 1; particular preference is given to compounds of the formula I in which R1 is described by hydrogen, methyl, ethyl, methoxy, ethoxy, F, Cl, —O—CF$_3$, —O—CH$_2$—CF$_3$ or —S—CF$_3$, in particular hydrogen, methyl, —O—CH$_2$—CF$_3$ or —S—CF$_3$. Specific preference is given to compounds in which R1 is described by hydrogen or methyl.

In a further embodiment, preference is given to compounds of the formula I in which R2 is described by hydrogen, methyl, methoxy, F, Cl, —O—CF$_3$, —O—CH$_2$—CF$_3$ or —S—CF$_3$, in particular hydrogen, F, Cl, O—CF$_3$, —O—CH$_2$—CF$_3$ or —S—CF$_3$, particular preference is given to compounds in which R2 is described by hydrogen.

In a further embodiment, preference is given to compounds of the formula I in which R3 is described by hydrogen, F, Cl, —CN, —SO$_2$CH$_3$, methoxy, ethoxy, —NR9R10, —O—CF$_3$, —O—CH$_2$—CF$_3$, SO$_2$CF$_3$, —S—CF$_3$, alkyl having 1, 2, 3 or 4 carbon atoms or cycloalkyl having 3, 4, 5 or 6 carbon atoms, in which 1, 2, 3 or 4 hydrogen atoms may be replaced by fluorine atoms, where R9 and R10 are independently of one another hydrogen, methyl, ethyl or —CH$_2$—CF$_3$, or by phenyl or —O-phenyl in which the phenyl radicals are unsubstituted or are substituted by 1, 2 or 3 radicals selected from the group consisting of series F, Cl, —O—CF$_3$, —O—CH$_2$—CF$_3$, —S—CF$_3$, methoxy, ethoxy, alkyl having 1, 2, 3 or 4 carbon atoms and —SO$_2$CH$_3$; particular preference is given to compounds in which R3 is described by F, Cl, —CN, —SO$_2$CH$_3$, —CF$_3$, —O—CF$_3$, —O—CH$_2$—CF$_3$, —SO$_2$CF$_3$, —S—CF$_3$, alkyl having 1, 2, 3 or 4 carbon atoms or cycloalkyl having 3, 4, 5 or 6 carbon atoms, in which 1, 2, 3 or 4 hydrogen atoms may be replaced by fluorine atoms; or by phenyl or —O-phenyl in which the phenyl radicals are unsubstituted or are substituted by 1 or 2 radicals selected from the group consisting of series F, Cl, —O—CF$_3$, —O—CH$_2$—CF$_3$, —S—CF$_3$, methoxy, ethoxy, alkyl having 1, 2, 3 or 4 carbon atoms and —SO$_2$CH$_3$; specific preference is given to compounds in which R3 is described by —CN, —SO$_2$CH$_3$, —CF$_3$, —O—CF$_3$, —O—CH$_2$—CF$_3$, —SO$_2$CF$_3$, —S—CF$_3$, in particular —SO$_2$CH$_3$ or —CF$_3$.

In a further embodiment, preference is given to compounds of the formula I in which R4 is described by hydrogen, F, Cl, —CN, —SO$_2$CH$_3$ or methyl, in particular hydrogen or F, particular preference is given to compounds in which R4 is described by hydrogen.

In a further embodiment, preference is given to compounds of the formula I in which R5 and R6 are described independently of one another by hydrogen, methyl or ethyl; particular preference is given to compounds in which R5 and R6 are described independently of one another by hydrogen or methyl, for example hydrogen.

In a further embodiment, preference is given to compounds of the formula I in which R7 and R8 are described independently of one another by hydrogen, alkyl having 1, 2, 3 or 4 carbon atoms, cycloalkyl having 3, 4, 5 or 6 carbon atoms, —CF$_3$ or phenyl, where the phenyl radical is unsubstituted or is substituted by 1, 2, or 3 radicals, for example by 1 or 2 radicals selected from the group consisting of series F, Cl, —O—CF$_3$, —O—CH$_2$—CF$_3$, —S—CF$_3$, methoxy, ethoxy, alkyl having 1, 2, 3 or 4 carbon atoms and —SO$_2$CH$_3$, or in which R7 and R8 form together with the carbon atom carrying them a cycloalkyl having 3, 4, 5 or 6 carbon atoms; particular preference is given to compounds in which R7 is described by hydrogen and R8 by alkyl having 1, 2, 3 or 4 carbon atoms, cycloalkyl having 3, 4, 5 or 6 carbon atoms, —CF₃ or phenyl, where the phenyl radical is unsubstituted or is substituted by 1 or 2 radicals selected from the group consisting of series F, Cl, —O—CF₃, —O—CH₂—CF₃, —S—CF₃, methoxy, ethoxy, alkyl having 1, 2, 3 or 4 carbon atoms and —SO₂CH₃; for example, R8 is described by phenyl which is unsubstituted or is substituted by 1 or 2 radicals selected from the group consisting of series F, Cl, —O—CF₃, —O—CH₂—CF₃, —S—CF₃, methoxy, ethoxy, alkyl having 1, 2, 3 or 4 carbon atoms and —SO₂CH₃, in particular F. In a further embodiment, preference is given to compounds in which R7 and R8 are hydrogen.

In a further embodiment, preference is given to compounds of the formula I in which X is described by —CH₂— or —NR17-, where R17 is hydrogen, methyl, ethyl, cycloalkyl having 3, 4, 5 or 6 carbon atoms, —CH₂—CF₃ or phenyl which is unsubstituted or is substituted by 1, 2 or 3 radicals selected from the group consisting of F, Cl, Br, I, —O—CF₃, —O—CH₂—CF₃, —S—CF₃, methoxy, ethoxy, alkyl having 1, 2, 3 or 4 carbon atoms and —SO₂CH₃; R17 is preferably hydrogen, methyl, ethyl, cycloalkyl having 3, 4, 5 or 6 carbon atoms, —CH₂—CF₃ or phenyl which is unsubstituted or is substituted by 1, 2 or 3 radicals selected from the group consisting of F, Cl, Br, I, —O—CF₃, —O—CH₂—CF₃, —S—CF₃, methoxy, ethoxy, alkyl having 1, 2, 3 or 4 carbon atoms and —SO₂CH₃; R17 is particularly preferably described by hydrogen, methyl, ethyl, cycloalkyl having 3, 4, 5 or 6 carbon atoms or —CH₂—CF₃; R17 is for example described by cycloalkyl having 3, 4, 5 or 6 carbon atoms, for example cyclopropyl. In a further embodiment, X is preferably —CH₂—.

In a further embodiment, preference is given to compounds of the formula I in which Y is described by a bond or —CH₂—.

Specific preference is given to compounds of the formula I selected from the group:

N-[4-(1,1-dioxoisothiazolidin-2-yl)-5-methanesulfonyl-2-methylbenzoyl]-guanidine,
N-[4-(1,1-dioxo-[1,2]thiazinan-2-yl)-5-methanesulfonyl-2-methylbenzoyl]-guanidine,
N-[4-(3,3-dimethyl-1,1-dioxoisothiazolidin-2-yl)-5-methanesulfonyl-2-methylbenzoyl]guanidine,
N-[4-(1,1-dioxo-4-phenylisothiazolidin-2-yl)-5-methanesulfonyl-2-methyl-benzoyl]guanidine,
N-{4-[4-(4-fluorophenyl)-1,1-dioxoisothiazolidin-2-yl]-5-methanesulfonyl-2-methylbenzoyl}guanidine,
N-[4-(1,1-dioxo-4-phenyl-1-[1,2]thiazinan-2-yl)-5-methanesulfonyl-2-methyl-benzoyl]guanidine,
N-[4-(5-cyclopropyl-1,1-dioxo-1-[1,2,5]thiadiazolidin-2-yl)-5-methanesulfonyl-2-methylbenzoyl]guanidine,
N-[4-(6-cyclopropyl-1,1-dioxo-1-[1,2,6]thiadiazinan-2-yl)-5-methanesulfonyl-2-methylbenzoyl]guanidine,
N-[4-(1,1-dioxo-1-isothiazolidin-2-yl)-3-trifluoromethyl-benzoyl]guanidine,
N-[4-(1,1-dioxo-1-[1,2]thiazinan-2-yl)-3-trifluoromethyl-benzoyl]guanidine and the pharmaceutically acceptable salts thereof.

If the substituents R1 to R8 contain one or more centers of asymmetry, these may independently of one another have both the S and the R configuration. The compounds may be in the form of optical isomers, of diastereomers, of racemates or of mixtures thereof.

The present invention encompasses all tautomeric forms of the compounds of the formula I.

Alkyl radicals may be straight-chain or branched. This also applies if they carry substituents or occur as substituents of other radicals, for example in fluoroalkyl radicals or alkoxy radicals. Examples of alkyl radicals are methyl, ethyl, n-propyl, isopropyl (=1-methylethyl), n-butyl, isobutyl (=2-methylpropyl), sec-butyl (=1-methylpropyl), tert-butyl (=1,1-dimethylethyl), n-pentyl, isopentyl, tert-pentyl, neopentyl and hexyl. Preferred alkyl radicals are methyl, ethyl, n-propyl and isopropyl. One or more, for example 1, 2, 3, 4 or 5, hydrogen atoms in alkyl radicals may be replaced by fluorine atoms. Examples of such fluoroalkyl radicals are trifluoromethyl, 2,2,2-trifluoroethyl and pentafluoroethyl. Substituted alkyl radicals may be substituted in any positions.

Examples of cycloalkyl radicals are cyclopropyl, cyclobutyl, cyclopentyl, cyclohexyl, cycloheptyl or cyclooctyl. One or more, for example 1, 2, 3 or 4, hydrogen atoms in cycloalkyl radicals may be replaced by fluorine atoms. Substituted cycloalkyl radicals may be substituted in any positions.

Phenyl radicals may be unsubstituted or be substituted one or more times, for example once, twice or three times, by identical or different radicals. If a phenyl radical is substituted, it preferably has one or two identical or different substituents. This likewise applies to substituted phenyl radicals in groups such as, for example, phenylalkyl or phenyloxy. The substituent in monosubstituted phenyl radicals may be in the 2 position, the 3 position or the 4 position. Disubstituted phenyl may be substituted in the 2,3 position, 2,4 position, 2,5 position, 2,6 position, 3,4 position or 3,5 position. The substituents in trisubstituted phenyl radicals may be in the 2,3,4 position, 2,3,5 position, 2,4,5 position, 2,4,6 position, 2,3,6 position or 3,4,5 position.

Heteroaryl radicals are aromatic ring compounds in which one or more ring atoms are oxygen atoms, sulfur atoms or nitrogen atoms, e.g. 1, 2 or 3 nitrogen atoms, 1 or 2 oxygen atoms, 1 or 2 sulfur atoms or a combination of various heteroatoms. The heteroaryl radicals may be attached by all positions, for example by the 1 position, 2 position, 3 position, 4 position, 5 position, 6 position, 7 position or 8 position. Heteroaryl radicals may be unsubstituted or be substituted one or more times, for example once, twice or three times, by identical or different radicals. This applies likewise to heteroaryl radicals such as, for example, in the radical heteroarylalkyl. Examples of heteroaryl are furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl and cinnolinyl.

Heteroaryl radicals are, in particular, 2- or 3-thienyl, 2- or 3-furyl, 1-, 2- or 3-pyrrolyl, 1-, 2-, 4- or 5-imidazolyl, 1-, 3-, 4- or 5-pyrazolyl, 1,2,3-triazol-1-, -4- or -5-yl, 1,2,4-triazol-1-, -3- or -5-yl, 1- or 5-tetrazolyl, 2-, 4- or 5-oxazolyl, 3-, 4- or 5-isoxazolyl, 1,2,3-oxadiazol-4- or -5-yl, 1,2,4-oxadiazol-3- or -5-yl, 1,3,4-oxadiazol-2-yl or -5-yl, 2-, 4- or 5-thiazolyl, 3-, 4- or 5-isothiazolyl, 1,3,4-thiadiazol-2- or -5-yl, 1,2,4-thiadiazol-3- or -5-yl, 1,2,3-thiadiazol-4- or -5-yl, 2-, 3- or 4-pyridyl, 2-, 4-, 5- or 6-pyrimidinyl, 3- or 4-pyridazinyl, pyrazinyl, 1-, 2-, 3-, 4-, 5-, 6- or 7-indolyl, 1-, 2-, 4- or 5-benzimidazolyl, 1-, 3-, 4-, 5-, 6- or 7-indazolyl, 2-, 3-, 4-, 5-, 6-, 7- or 8-quinolyl, 1-, 3-, 4-, 5-, 6-, 7- or 8-isoquinolyl, 2-, 4-, 5-, 6-, 7- or 8-quinazolinyl, 3-, 4-, 5-, 6-, 7- or 8-cinnolinyl, 2-, 3-, 5-, 6-, 7- or 8-quinoxalinyl, 1-, 4-, 5-, 6-, 7- or 8-phthalazinyl. Also encompassed are the corresponding N-oxides of these compounds, i.e. for example 1-oxy-2-, -3- or 4-pyridyl.

Particularly preferred heteroaromatic radicals are 2- or 3-thienyl, 2- or 3-furyl, 1-, 2- or 3-pyrrolyl, 1-, 2-, 4- or 5-imidazolyl, 2-, 3-, 4-, 5-, 6-, 7- or 8-quinolyl, 1-, 3-, 4- or 5-pyrazolyl, 2-, 3- or 4-pyridyl, 2- or 3-pyrazinyl, 2-, 4-, 5- or 6-pyrimidinyl and 3- or 4-pyridazinyl.

The invention further relates to a process for preparing the compounds of the formula I which comprises reacting a compound of the formula II

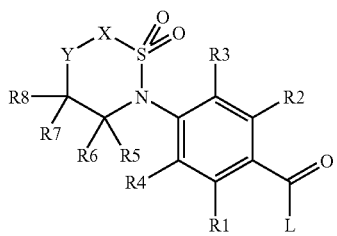

in which R1 to R8 have the meaning as in compounds of the formula I, and L is a leaving group which can undergo nucleophilic substitution, with guanidine.

The activated acid derivatives of the formula II in which L is an alkoxy, preferably a methoxy, group, a phenoxy group, phenylthio, methylthio, 2-pyridylthio group, a nitrogen heterocycle, preferably 1-imidazolyl, are advantageously obtained in a manner known to those skilled in the art from the underlying carbonyl chlorides (formula II; L=Cl), which in turn can themselves be prepared in a known manner from the underlying carboxylic acids (formula II; L=OH), for example using thionyl chloride.

Besides the carbonyl chlorides of the formula II (L=Cl) it is also possible to prepare other activated acid derivatives of the formula II in a known manner directly from the underlying benzoic acids (formula II; L=OH), such as the methyl esters of the formula II with L=OCH$_3$ by treatment with gaseous HCl in methanol, the imidazolides of the formula II by treatment with carbonyldiimidazole, the mixed anhydrides of the formula II by treatment with Cl—COOC$_2$H$_5$ or tosyl chloride in the presence of triethylamine in an inert solvent, as activations of benzoic acids with dicyclohexylcarbodiimide (DCC) or with O-[(cyano(ethoxycarbonyl)-methylene)amino]-1,1,3,3-tetramethyluronium tetrafluoroborate ("TOTU") are also possible. A number of suitable methods for preparing activated carboxylic acid derivatives of the formula II are indicated in J. March, Advanced Organic Chemistry, third edition (John Wiley & Sons, 1985, page 350), indicating source literature.

Reaction of an activated carboxylic acid derivative of the formula II with guanidine preferably takes place in a known manner in a protic or aprotic polar but inert organic solvent. Those which have proved suitable for the reaction of the methyl benzoates (formula II; L=OCH$_3$) with guanidine are methanol, isopropanol or THF at temperatures from 20° C. to the boiling point of these solvents. Most reactions of compounds of the formula II with salt-free guanidine are, for example, carried out in aprotic inert solvents such as THF, dimethoxyethane, dioxane. However, it is also possible to use water in the presence of a base such as, for example, NaOH as solvent in the reaction of compounds of the formula II with guanidine.

If L is Cl, it is advantageous to add an acid scavenger, for example in the form of excess guanidine, to bind the hydrohalic acid.

In one embodiment, preference is given to compounds of the formula II in which L is described by alkoxy having 1, 2, 3 or 4 carbon atoms, benzyloxy, phenoxy, phenylthio, methylthio, 2-pyridylthio, nitrogen heterocycle, for example 1-imidazolyl, F, Cl, Br, I or OH; particular preference is given to compounds of the formula II in which L is described by methoxy, Cl or OH.

The invention further relates to a process for preparing the compounds of the formula II,

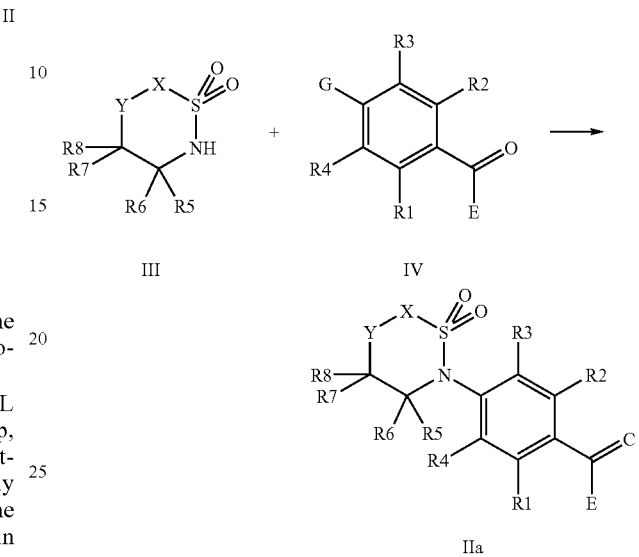

which comprises reacting a compound of the formula III with a compound of the formula IV in a nucleophilic aromatic substitution to give a compound of the formula IIa, in which R1 to R8, X and Y have the indicated meaning, and E is alkoxy having 1, 2, 3 or 4 carbon atoms, benzyloxy or phenoxy;

G is F, Cl, Br or I;

A compound of the formula III is in this case reacted with a compound of the formula IV together with an inorganic base, preferably K$_2$CO$_3$ or Cs$_2$CO$_3$, or an organic base, preferably TBTMG in a dipolar aprotic solvent, preferably DMF or NMP at a temperature of between −40° C. and the boiling point of the solvent, preferably between 0° C. and 140° C., to give the compounds of the formula IV.

An ester of the formula IIa is reallocated further to give compounds of the formula II, for example hydrolyzed to the acid of the formula II (L=OH) or converted by methods known to the skilled worker into an acid chloride of the formula II (L=Cl).

Sultams and cyclic sulfamides of the formula III can be synthesized in analogy to known methods (Pharmaceutical Chemistry Journal (translation of Khimiko-Farmatsevticheskii Journal) (2000), volume date 1999, 33(11), 598; J. Org. Chem. (1991), 56, 3549; Tetrahedron 59, (2003) 6051).

Compounds of the formula IV can be synthesized in analogy to known methods as described for example in J. Chem. Soc., Chem. Commun., 1993, 1359; J. Med. Chem. 1998, 41, 3736; J. Med. Chem. 1997, 40, 2017; Bioorg. Med. Chem. Left. 13 (2003), 4085; Eur. J. Org. Chem. 2002, 1490.

Functional groups in the starting compounds may also be in protected form or in the form of precursors, and can then be converted into the desired groups in the compounds of the formula II prepared by the process described above. Appropriate protective group techniques are known to the skilled worker.

It is likewise possible to derivatize appropriate functional groups by methods known to the skilled worker.

The invention further relates to compounds of the formula II:

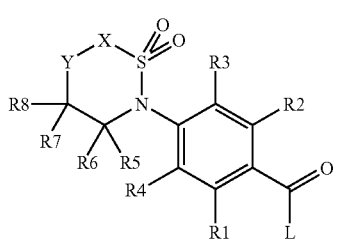

in which R1 to R8, X and Y are defined as in compounds of the formula I, and L is defined as described above,
excepting compounds of the formula II in which R1, R2, R3 and R4 are simultaneously hydrogen, and X is —CH$_2$—, and excluding the following compounds
methyl 4-(1,1-dioxoisothiazolidin-2-yl)-3-methylbenzoate,
4-(1,1-dioxoisothiazolidin-2-yl)-3-methylbenzoic acid,
methyl 4-(1,1-dioxo-1-[1,2,6]thiadiazinan-2-yl)-3-methylbenzoate,
4-(1,1-dioxo-1-[1,2,6]thiadiazinan-2-yl)-3-methylbenzoic acid
and
3-chloro-4-(1,1-dioxo-1-[1,2]thiazinan-2-yl)benzoic acid.

Benzoylguanidines of the formula I and compounds of the formula II are generally weak bases and are able to bind acid to form salts. Suitable acid addition salts are salts of all pharmaceutically acceptable acids, for example halides, in particular hydrochlorides, lactates, sulfates, citrates, tartrates, acetates, phosphates, methylsulfonates, p-toluenesulfonates.

The compounds of the formula I are substituted acylguanidines and inhibit the cellular sodium-proton antiporter (Na$^+$/H$^+$ exchanger, NHE), in particular the subtype NHE-1.

Compared with known NHE inhibitors, the compounds of the invention are distinguished by an exceptionally high activity in inhibiting Na$^+$/H$^+$ exchange, and by improved ADMET properties, for example by longer S9 stabilities (liver stabilities, stability to enzymatic attack) and high selectivity in relation to the hERG potassium channel. They moreover show a good absorption behavior and a high bioavailability.

Because of the NHE-inhibitory properties, the compounds of the formula I and/or the pharmaceutically acceptable salts thereof are suitable for the prevention and treatment of diseases caused by activation or by an activated NHE, and of diseases caused secondarily by the NHE-related damage.

Since NHE inhibitors predominantly act via their effect on cellular pH regulation, they can generally be combined beneficially with other compounds which regulate the intracellular pH, with suitable combination partners being inhibitors of the carbonic anhydrase enzyme group, inhibitors of systems transporting bicarbonate ions, such as of the sodium bicarbonate cotransporter (NBC) or of the sodium-dependent chloride-bicarbonate exchanger (NCBE), and NHE inhibitors with inhibitory effect on other NHE subtypes, because it is possible through them to enhance or modulate the pharmacologically relevant pH-regulating effects of the NHE inhibitors described herein.

The use of the compounds of the invention relates to the prevention and treatment of acute and chronic diseases in veterinary and human medicine.

Thus, the NHE inhibitors of the invention are suitable for the treatment of diseases caused by ischemia and by reperfusion.

The compounds described herein are suitable because of their pharmacological properties as antiarrhythmic medicaments.

Owing to their cardioprotective component, the NHE inhibitors are outstandingly suitable for infarction prophylaxis and infarction treatment and for the treatment of angina pectoris, in which cases they also preventively inhibit or greatly reduce the pathophysiological processes associated with the development of ischemia-induced damage, in particular in the triggering of ischemia-induced cardiac arrhythmias. Because of their protective effects against pathological hypoxic and ischemic situations, the compounds of the formula I and/or the pharmaceutically acceptable salts thereof used according to the invention can, because of inhibition of the cellular Na$^+$/H$^+$ exchange mechanism, be used as medicaments for the treatment of all acute or chronic ischemia-induced damage or diseases induced primarily or secondarily thereby.

This also relates to their use as medicaments for surgical interventions. Thus, the compounds can be used during organ transplantations, it being possible to use the compounds both to protect the organs in the donor before and during the removal, to protect removed organs, for example during treatment with or storage thereof in physiological bath liquids, and during transference into the recipient organism.

The compounds of the invention are likewise valuable medicaments with a protective effect when performing angioplastic surgical interventions, for example on the heart as well as on peripheral organs and vessels.

The compounds of the invention may also be used when performing bypass operations, for example bypass operations on coronary vessels and in coronary artery bypass graft (CABG).

Depending on their activity with regard to ischemia-induced damage, the compounds of the invention of the formula I may similarly be used in resuscitation after a cardiac arrest.

The compounds of the invention are of interest for medicaments for life-threatening arrhythmias. Ventricular fibrillation is terminated and the physiological sinus rhythm of the heart is restored.

Since NHE1 inhibitors of human tissue and organs, especially the heart, protect effectively not only against damage caused by ischemia and reperfusion but also against the cytotoxic effect of medicaments like those used in particular in cancer therapy and the therapy of autoimmune diseases, combined administration with compounds of the formula I and/or the pharmaceutically acceptable salts thereof is suitable for inhibiting the cytotoxic, especially cardiotoxic, side effects of said compounds. The reduction in the cytotoxic effects, especially the cardiotoxicity, resulting from comedication with NHE1 inhibitors makes it additionally possible to increase the dose of the cytotoxic therapeutic agents and/or to prolong the medication with such medicaments. The therapeutic benefits of such a cytotoxic therapy can be considerably increased by combination with NHE inhibitors.

In addition, the NHE1 inhibitors of the invention of the formula I and/or the pharmaceutically acceptable salts thereof can be used when there is heart-damaging overproduction of thyroid hormones, thyrotoxicosis, or on external supply of thyroid hormones. The compounds of the formula I and/or the pharmaceutically acceptable salts thereof are thus suitable for improving therapy with cardiotoxic medicaments.

In accordance with their protective effect against ischemia-induced damage, the compounds of the invention are also suitable as medicaments for the treatment of ischemias of the nervous system, especially of the central nervous system, being suitable for example for the treatment of stroke or of cerebral edema.

The compounds of the formula I and/or the pharmaceutically acceptable salts thereof are also suitable for the therapy and prophylaxis of diseases and disorders induced by overexcitability of the central nervous system, in particular for the treatment of epileptic disorders, centrally induced clonic and tonic spasms, states of psychological depression, anxiety disorders and psychoses. In these cases it is possible to use the NHE inhibitors described herein alone or in combination with other substances with antiepileptic activity or antipsychotic active ingredients, or carbonic anhydrase inhibitors, for example with acetazolamide, and with other inhibitors of NHE or of the sodium-dependent chloride-bicarbonate exchanger (NCBE).

The compounds used according to the invention of the formula I and/or the pharmaceutically acceptable salts thereof are additionally likewise suitable for the treatment of types of shock such as, for example, of allergic, cardiogenic, hypovolemic and bacterial shock.

The compounds of the formula I and/or the pharmaceutically acceptable salts thereof can likewise be used for the prevention and treatment of thrombotic disorders because they, as NHE inhibitors, are able to inhibit platelet aggregation themselves. They are additionally able to inhibit or prevent the excessive release, occurring after ischemia and reperfusion, of mediators of inflammation and coagulation, especially of von Willebrand factor and of thrombogenic selectin proteins. It is thus possible to reduce and eliminate the pathogenic effect of significant thrombogenic factors. The NHE inhibitors of the present invention can therefore be combined with other anticoagulant and/or thrombolytic active ingredients such as, for example, recombinant or natural tissue plasminogen activator, streptokinase, urokinase, acetylsalicylic acid, thrombin antagonists, factor Xa antagonists, medicinal substances with fibrinolytic activity, thromboxane receptor antagonists, phosphodiesterase inhibitors, factor VIIa antagonists, clopidogrel, ticlopidine etc. Combined use of the present NHE inhibitors with NCBE inhibitors and/or with inhibitors of carbonic anhydrase such as, for example, with acetazolamide, is particularly beneficial.

NHE1 inhibitors are additionally distinguished by a strong inhibitory effect on the proliferation of cells, for example fibroblast proliferation and the proliferation of smooth vascular muscle cells. The compounds of the formula I and/or the pharmaceutically acceptable salts thereof are therefore suitable as valuable therapeutic agents for diseases in which proliferation represents a primary or secondary cause, and can therefore be used as antiatherosclerotics, agents for chronic renal failure, cancers.

It was possible to show that cell migration is inhibited by NHE inhibitors. The compounds of the formula I and/or the pharmaceutically acceptable salts thereof are therefore suitable as valuable therapeutic agents for diseases in which cell migration represents a primary or secondary cause, such as, for example, cancers with a pronounced tendency to metastasis.

NHE1 inhibitors are further distinguished by a retardation or prevention of fibrotic disorders. Compounds of the formula I and/or the pharmaceutically acceptable salts thereof are thus suitable as agents for the treatment of cardiac fibroses, and of pulmonary fibrosis, hepatic fibrosis, renal fibrosis and other fibrotic disorders. They can thus be used for the treatment of organ hypertrophies and hyperplasias, for example of the heart and the prostate. They are therefore suitable for the prevention and treatment of heart failure (congestive heart failure=CHF) and for the treatment and prevention of prostate hyperplasia or prostate hypertrophy.

Since there is significant elevation in NHE in essential hypertensives, the compounds of the formula I and/or the pharmaceutically acceptable salts thereof are suitable for the prevention and treatment of high blood pressure and for the treatment of cardiovascular disorders. In these cases, they can be used alone or with a suitable combination and formulation partner for the treatment of high blood pressure and of cardiovascular disorders. Thus, for example, one or more diuretics with a thiazide-like action, loop diuretics, aldosterone and pseudoaldosterone antagonists, such as hydrochlorothiazide, indapamide, polythiazide, furosemide, piretanide, torasemide, bumetanide, amiloride, triamterene, spironolactone or eplerone, can be combined. The NHE inhibitors of the present invention can further be used in combination with calcium channel blockers such as verapamil, diltiazem, amlodipine or nifedipine, and with ACE inhibitors such as, for example, ramipril, enalapril, lisinopril, fosinopril or captopril. Further beneficial combination partners are also β-blockers such as metoprolol, albuterol etc., antagonists of the angiotensin receptor and its receptor subtypes such as losartan, irbesartan, valsartan, omapatrilat, gemopatrilat, endothelin antagonists, renin inhibitors, adenosine receptor agonists, inhibitors and activators of potassium channels such as glibenclamide, glimepiride, diazoxide, cromakalim, minoxidil and derivatives thereof, activators of the mitochondrial ATP-sensitive potassium channel (mitoK(ATP) channel), inhibitors of Kv1.5 etc.

It has emerged that NHE1 inhibitors have a significant antiinflammatory effect and can thus be used as antiinflammatory drugs. Inhibition of the release of mediators of inflammation is noteworthy in this connection. The compounds can thus be used alone or in combination with an antiinflammatory drug for the prevention or treatment of chronic and acute inflammatory disorders. Combination partners advantageously used are steroidal and non-steroidal antiinflammatory drugs. The compounds of the invention can additionally be employed for the prevention or treatment of disorders caused by protozoa, such as malaria and coccidiosis in poultry.

It has additionally been found that NHE1 inhibitors show a beneficial effect on serum lipoproteins. It is generally acknowledged that blood fat levels which are too high, so-called hyperlipoproteinemias, represent an essential risk factor for the development of arteriosclerotic vascular lesions, especially coronary heart disease. The reduction of elevated serum lipoproteins therefore has exceptional importance for the prophylaxis and regression of atherosclerotic lesions. Besides the reduction in total serum cholesterol, it is particularly important to reduce the proportion of specific atherogenic lipid fractions of this total cholesterol, in particular of the low density lipoproteins (LDL) and of the very low density lipoproteins (VLDL), because these lipid fractions represent an atherogenic risk factor. By contrast, a protective function against coronary heart disease is ascribed to the high density lipoproteins. Accordingly, hypolipidemics should be able to reduce not only total cholesterol but, in particular, the VLDL and LDL serum cholesterol fractions. It has now been found that NHE1 inhibitors show valuable therapeutically utilizable properties in relation to influencing the serum lipid levels. Thus, they significantly reduce the elevated serum concentrations of LDL and VLDL as are to be observed, for example, due to increased dietary intake of a cholesterol- and lipid-rich diet or in cases of pathological metabolic alterations, for example genetically related hyperlipidemias. They can therefore be used for the prophylaxis and regression of atherosclerotic lesions by eliminating a causal risk factor. Included herein are not only the primary hyperlipidemias but also certain secondary hyperlipidemias occurring, for example, in association with diabetes. In addition, the NHE1 inhibitors lead to a marked reduction in the infarctions induced by metabolic abnormalities and, in particular, to a significant reduction in the induced infarct size and the severity thereof.

The compounds of the formula I and/or the pharmaceutically acceptable salts thereof are therefore advantageously used for producing a medicament for the treatment of hypercholesterolemia; for producing a medicament for the prevention of atherogenesis; for producing a medicament for the prevention and treatment of atherosclerosis, for producing a medicament for the prevention and treatment of diseases induced by elevated cholesterol levels, for producing a medicament for the prevention and treatment of diseases induced by endothelial dysfunction, for producing a medicament for the prevention and treatment of atherosclerosis-induced hypertension, for producing a medicament for the prevention and treatment of atherosclerosis-induced thromboses, for producing a medicament for the prevention and treatment of hypercholesterolemia-induced and endothelial dysfunction-induced ischemic damage and post-ischemic reperfusion damage, for producing a medicament for the prevention and treatment of hypercholesterolemia-induced and endothelial dysfunction-induced cardiac hypertrophies and cardiomyopathies and of congestive heart failure (CHF), for producing a medicament for the prevention and treatment of hypercholesterolemia-induced and endothelial dysfunction-induced coronary vasospasms and myocardial infarctions, for producing a medicament for the treatment of said disorders in combinations with hypotensive substances, preferably with angiotensin converting enzyme (ACE) inhibitors and angiotensin receptor antagonists. A combination of an NHE inhibitor of the formula I and/or the pharmaceutically acceptable salts thereof with an active ingredient lowering the blood fat levels, preferably with an HMG-CoA reductase inhibitor (for example lovastatin or pravastatin), the latter bringing about a hypolipidemic effect and thus increasing the hypolipidemic properties of the NHE inhibitor of the formula I and/or the pharmaceutically acceptable salts thereof, proves to be a favorable combination with enhanced effect and reduced use of active ingredients.

Thus, compounds of the formula I and/or the pharmaceutically acceptable salts thereof lead to effective protection against endothelial damage of various origins. This protection of the vessels against the syndrome of endothelial dysfunction means that compounds of the formula I and/or the pharmaceutically acceptable salts thereof are valuable medicaments for the prevention and treatment of coronary vasospasms, peripheral vascular diseases, in particular intermittent claudication, atherogenesis and atherosclerosis, left ventricular hypertrophy and dilated cardiomyopathy and thrombotic disorders.

It has additionally been found that NHE1 inhibitors are suitable in the treatment of non-insulin-dependent diabetes (NIDDM), with the insulin resistance being restrained. It may in this connection be beneficial, to enhance the antidiabetic activity and quality of the effect of the compounds of the invention, to combine them with a biguanide such as metformin, with an antidiabetic sulfonylurea such as glyburide, glimepiride, tolbutamide etc., with a glucosidase inhibitor, with a PPAR agonist such as rosiglitazone, pioglitazone etc., with an insulin product of different administration form, with a DB4 inhibitor, with an insulin sensitizer or with meglitinide.

Besides the acute antidiabetic effects, the compounds of the formula I and/or the pharmaceutically acceptable salts thereof counteract the development of late complications of diabetes and can therefore be used as medicaments for the prevention and treatment of late damage from diabetes, such as diabetic nephropathy, diabetic neuropathy, diabetic retinopathy, diabetic cardiomyopathy and other disorders occurring as a consequence of diabetes. They can in this connection be advantageously combined with the antidiabetic medicaments just described under NIDDM treatment. The combination with a beneficial dosage form of insulin should be particularly important in this connection.

NHE1 inhibitors show, besides the protective effects against acute ischemic events and the subsequent equally acutely stressing reperfusion events, also direct therapeutically utilizable effects against diseases and disorders of the entire mammalian organism which are associated with the manifestations of the chronically progressive aging process and which occur independently of acute hypoperfusion states and under normal, non-ischemic conditions. These pathological, age-related manifestations induced over the long aging period, such as illness, invalidity and death, which can now be made amenable to treatment with NHE inhibitors, are diseases and disorders which are essentially caused by age-related changes in vital organs and the function thereof and become increasingly important in the aging organism.

Disorders connected with an age-related functional impairment or with age-related manifestations of wear of organs are, for example, the inadequate response and reactivity of the blood vessels to contraction and relaxation reactions. This age-related decline in the reactivity of vessels to constricting and relaxing stimuli, which are an essential process of the cardiovascular system and thus of life and health, can be significantly eliminated or reduced by NHE inhibitors. One important function and a measure of the maintenance of the reactivity of vessels is the blockade or retardation of the age-related progression in endothelial dysfunction, which can be eliminated highly significantly by NHE inhibitors. The compounds of the formula I and/or the pharmaceutically acceptable salts thereof are thus outstandingly suitable for the treatment and prevention of the age-related progression in endothelial dysfunction, especially of intermittent claudication.

An example of another variable characterizing the aging process is the decline in the contractility of the heart and the decline in the adaptation of the heart to a required pumping output of the heart. This diminished efficiency of the heart as a consequence of the aging process is in most cases connected with a dysfunction of the heart which is caused inter alia by deposition of connective tissue in the myocardial tissue. This deposition of connective tissue is characterized by an increase in the weight of the heart, by an enlargement of the heart and by restrictive cardiac function. It was surprising that it was possible almost completely to inhibit such aging of the heart organ. The compounds of the formula I and/or the pharmaceutically acceptable salts thereof are thus outstandingly suitable for the treatment and prevention of heart failure, of congestive heart failure (CHF).

Not only is it possible to cure a cancer which has already occurred through inhibition of proliferation, but there is also reduction and highly significant retardation of the age-related incidence of cancer through NHE inhibitors. A particularly noteworthy finding is that the disorders, occurring as a result of aging, of all organs and not only certain types of cancer are suppressed or occur with a highly significant delay. The compounds of the formula I and/or the pharmaceutically acceptable salts thereof are thus suitable for the treatment and, in particular, the prevention of age-related types of cancer.

With NHE inhibitors, a delay, shifted highly significantly in time is found in the occurrence of age-related disorders of all the organs investigated, including the heart, vessels, liver etc., and a highly significant delay in cancer of the elderly. On the contrary, there is also surprisingly a prolongation of life to an extent which has to date been achievable by no other group of medicaments or by any natural products. This unique effect of NHE inhibitors also makes it possible, besides the use of the active ingredients alone on humans and animals, to combine these NHE inhibitors with other active principles, measures, substances and natural products which are used in gerontology and which are based on a different mechanism of action. Such classes of active ingredients used in gerontological therapy are: in particular vitamins and substances with antioxidant activity. Since there is a correlation between caloric load or food intake and the aging process, the combination with dietary measures can take place for example with appetite suppressants. It is likewise possible to consider a combination with hypotensive medicaments such as with ACE inhibitors, angiotensin receptor antagonists, diuretics, $Ca^{+2}$ antagonists etc. or with metabolism-normalizing medicaments such as cholesterol-lowering agents.

The compounds of the formula I and/or the pharmaceutically acceptable salts thereof are thus outstandingly suitable for the prevention of age-related tissue changes and for prolonging life while retaining a high quality of life.

The compounds of the invention are effective inhibitors of the cellular sodium-proton antiporter (Na/H exchanger) which in a large number of disorders (essential hypertension, atherosclerosis, diabetes etc.) is also increased in cells which are readily amenable to measurements, such as, for example, in erythrocytes, platelets or leucocytes. The compounds used according to the invention are therefore suitable as outstanding and simple scientific tools, for example in their use as diagnostic agents for determining and distinguishing different types of hypertension, but also of atherosclerosis, diabetes and the late complications of diabetes, proliferative disorders etc.

Also claimed is a medicine for human, veterinary or phytoprotective use, comprising an effective amount of a compound of the formula I and/or the pharmaceutically acceptable salts thereof, together with pharmaceutically acceptable carriers and additives, alone or in combination with other pharmacological active ingredients or medicaments.

Medicaments which comprise a compound of the formula I and/or the pharmaceutically acceptable salts thereof can in this connection be administered, for example, orally, parenterally, intravenously, rectally, transdermally or by inhalation, the preferred administration being dependent on the particular characteristics of the disorder. The compounds of the formula I may moreover be used alone or together with pharmaceutical excipients, both in veterinary medicine and in human medicine. The medicaments generally comprise active ingredients of the formula I and/or the pharmaceutically acceptable salts thereof in an amount of from 0.01 mg to 1 g per dose unit.

The excipients suitable for the desired pharmaceutical formulation are familiar to the skilled worker on the basis of his expert knowledge. Besides solvents, gel formers, suppository bases, tablet excipients, and other active ingredient carriers, it is possible to use, for example, antioxidants, dispersants, emulsifiers, antifoams, flavorings, preservatives, solubilizers or colors.

For a form for oral administration, the active compounds are mixed with additives suitable for this purpose, such as carriers, stabilizers or inert diluents, and converted by conventional methods into suitable dosage forms such as tablets, coated tablets, hard gelatin capsules, aqueous, alcoholic or oily solutions. Examples of inert carriers which can be used are gum arabic, magnesia, magnesium carbonate, potassium phosphate, lactose, glucose or starch, especially corn starch. It is moreover possible for the preparation to take place both as dry granules and as wet granules. Examples of suitable oily carriers or solvents are vegetable or animal oils such as sunflower oil or fish liver oil.

For subcutaneous, intramuscular or intravenous administration, the active compounds used are converted, if desired with the substances customary for this purpose, such as solubilizers, emulsifiers or other excipients, into a solution, suspension or emulsion. Examples of suitable solvents are: water, physiological saline or alcohols, e.g. ethanol, propanol, glycerol, as well as sugar solutions such as glucose or mannitol solutions, or else a mixture of the various solvents mentioned.

Suitable as pharmaceutical formulation for administration in the form of aerosols or sprays are, for example, solutions, suspensions or emulsions of the active ingredient of the formula I and/or the pharmaceutically acceptable salts thereof in a pharmaceutically acceptable solvent such as, in particular, ethanol or water, or a mixture of such solvents. The formulation may, if required, also contain other pharmaceutical excipients such as surfactants, emulsifiers and stabilizers, and a propellant gas. Such a preparation normally contains the active ingredient in a concentration of about 0.1 to 10, in particular of about 0.3 to 3% by weight.

The dosage of the active ingredient of the formula I to be administered, and the frequency of administration, depend on the potency and duration of action of the compounds used; additionally also on the nature and severity of the disorder to be treated and on the sex, age, weight and individual responsiveness of the mammal to be treated.

On average, the daily dose of a compound of the formula I and/or the pharmaceutically acceptable salts thereof for a patient weighing about 75 kg is at least 0.001 mg/kg, for example 0.01 mg/kg, to a maximum of 10 mg/kg, for example 1 mg/kg, of body weight. For acute episodes of the disorder, for example immediately after suffering a myocardial infarction, higher and, in particular, more frequent dosages may also be necessary, e.g. up to 4 single doses a day. Up to 700 mg a day may be necessary, in particular on i.v. administration, for example for a patient with infarction in the intensive care unit, and the compounds of the invention can be administered by infusion.

DIP diisopropyl ether
DMF N,N-dimethylformamide
DMSO dimethyl sulfoxide
EA ethyl acetate
ES electron spray
KOtBu potassium 2-methylpropan-2-oleate
MeOH methanol
mp melting point
MTB tert-butyl methyl ether
NMP N-methyl-2-pyrrolidone
RT room temperature
TBTMG N"-tert-butyl-N,N,N',N'-tetramethylguanidine
THF tetrahydrofuran

Experimental Section

Example 1

N-[4-(1,1-Dioxoisothiazolidin-2-yl)-5-methanesulfonyl-2-methyl-benzoyl]guanidine

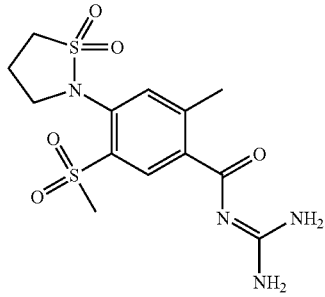

a) Methyl 4-(1,1-dioxo-1-isothiazolidin-2-yl)-5-methanesulfonyl-2-methylbenzoate 182 mg of isothiazolidine 1,1-dioxide (Journal of Organic Chemistry (1987), 52(11), 2162), 369 mg of methyl 4-fluoro-5-methanesulfonyl-2-methylbenzoate (Journal of Medicinal Chemistry (1997), 40(13), 2017) and 1.466 g of $Cs_2CO_3$ were stirred in 7.5 ml of anhydrous DMF for 4 hours and 30 minutes. The reaction mixture was then poured into 120 ml of a half-saturated aqueous $NaHCO_3$ solution and extracted 3 times with 80 ml of EA each time. After drying over $Na_2SO_4$, the solvent was removed in vacuo.
$R_f$(MTB)=0.44 MS (DCI): 348 b) N-[4-(1,1-Dioxoisothiazolidin-2-yl)-5-methanesulfonyl-2-methylbenzoyl]-guanidine 726 mg of guanidinium chloride were dissolved in 5 ml of anhydrous DMF and, at RT, a solution of 711 mg of KOtBU in 5 ml of anhydrous DMF was added. After stirring at RT for 10 minutes, a solution of 440 mg of methyl 4-(1,1-dioxo-1-isothiazolidin-2-yl)-5-methanesulfonyl-2-methylbenzoate in 5 ml of anhydrous DMF was added at RT. The mixture was then stirred at RT for 4 hours and 45 minutes, left to stand at RT for 16 hours and stirred at RT for a further 90 minutes. The reaction mixture was then poured into 120 ml of a half-saturated aqueous $NaHCO_3$ solution and extracted 3 times with 80 ml of EA each time. Drying over $Na_2SO_4$ and removal of the solvent in vacuo resulted in 367 mg of an amorphous solid.

Example 2

N-[4-(1,1-Dioxo-[1,2]thiazinan-2-yl)-5-methanesulfonyl-2-methylbenzoyl]guanidine

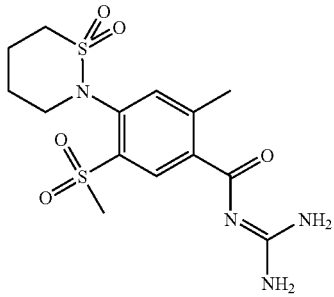

Example 2 was synthesized in analogy to Example 1.
$R_f$(EA)=0.50 MS (ES$^+$): 388

Example 3

N-[4-(3,3-Dimethyl-1,1-dioxoisothiazolidin-2-yl)-5-methanesulfonyl-2-methylbenzoyl]guanidine,

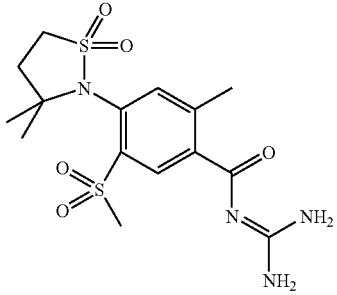

a) Phenyl 3-methyl-3-nitrobutane-1-sulfonate

A mixture of 9.43 g of phenyl ethenesulfonate and 4.60 ml of 2-nitro-propane was heated to 80° C. and, at 80° C., 0.89 ml of ethyidiisopropylamine was added dropwise. The mixture was stirred at 80° C. for 4 hours and 30 minutes, left to stand at RT for 16 hours and then stirred at 80° C. for a further 2 hours. Cooling to RT was followed by addition of 250 ml of a 2N aqueous HCl solution and extraction 3 times with 150 ml of EA each time. Drying over $Na_2SO_4$ and removal of the solvent in vacuo were followed by coevaporation 3 times with 100 ml of toluene each time. 13.47 g of a pale yellow oil were obtained.
$R_f$(EA/HEP 1:4)=0.23 b) Phenyl 3-amino-3-methylbutane-1-sulfonate 13.42 g of phenyl 3-methyl-3-nitrobutane-1-sulfonate were dissolved in 40 ml of MeOH, and 2.9 g of Raney nickel which had been washed until neutral were added. Hydrogenation was carried out under a pressure of 5 bar of hydrogen at RT for 20 hours. The catalyst was then filtered off and the solvent was removed in vacuo. 11.58 g of an amorphous solid were obtained.
$R_f$(EA/MeOH 5:1)=0.17 MS (DCI): 244 c) 3,3-Dimethylisothiazolidine 1,1-dioxide 11.58 g of phenyl 3-amino-3-methylbutane-1-sulfonate and 5.34 g of KOH were boiled under reflux in 240 ml of THF/95 ml of water for 7 hours. Then a further 2.7 g of KOH, 50 ml of water and 120 ml of THF were added, and the mixture was again boiled under reflux for 7 hour. Then a further 5.34 g of KOH were added, and the mixture was again boiled under reflux for 3 hours. It was allowed to cool and then 300 ml of a 2N aqueous HCl solution were added, and the mixture was extracted 5 times with 250 ml of EA each time. After drying over $Na_2SO_4$, the solvent was removed in vacuo. Chromatography on silica gel with EA/HEP 1:1 afforded 3.82 g of white crystals, mp 72° C.
$R_f$(EA/HEP 1:2)=0.14 MS (DCI): 150 d) Methyl 4-(3,3-dimethyl-1,1-dioxo-1-isothiazolidin-2-yl)-5-methanesulfonyl-2-methylbenzoate 339 mg of methyl 4-fluoro-5-methanesulfonyl-2-methylbenzoate (Journal of Medicinal Chemistry (1997), 40(13), 2017) and 206 mg of 3,3-dimethyl-isothiazolidine 1,1-dioxide were dissolved in 7 ml of anhydrous NMP and, at RT, 0.42 ml of N"-tert-butyl-N,N,N',N'-tetramethylguanidine was added. The mixture was stirred at 120° C. for 7 hours, then left to stand for 16 hours and thereafter again stirred at 120° C. for 1 hour and 30 minutes. The reaction mixture was allowed to cool and was then diluted with 120 ml of EA and washed 3 times with 80 ml of a 2N aqueous HCl solution each time, then 3 times with 80 ml of a saturated aqueous NaCO₃ solution each time and finally also once with 80 ml of a saturated aqueous Na₂Cl solution. After drying over Na₂SO₄, the solvent was removed in vacuo. Chromatography on Varian Polaris C18-A with water+0.1% trifluoroacetic acid/acetonitrile=9:1

Flow rate: T=0 minutes to T=3 minutes: 50 ml per minute
from T=3 minutes: 150 ml per minute
50 mg of a colorless oil were obtained at a retention time of 15.5 minutes.
MS (DCI): 376 e) N-[4-(3,3-Dimethyl-1,1-dioxoisothiazolidin-2-yl)-5-methanesulfonyl-2-methylbenzoyl]guanidine 69 mg of guanidinium chloride were dissolved in 2 ml of anhydrous DMF and, at RT, a solution of 67 mg of KOtBu in 2 ml of anhydrous DMF was added. After stirring at RT for 10 minutes, a solution of 45 mg of methyl 4-(3,3-dimethyl-1,1-dioxo-1-isothiazolidin-2-yl)-5-methanesulfonyl-2-methylbenzoate in 2 ml of anhydrous DMF was added at RT. The mixture was then stirred at RT for 3 hours, left to stand at RT for 16 hours and stirred at RT for a further 3 hours. The reaction mixture was then poured into 80 ml of a half-saturated aqueous NaHCO₃ solution and extracted 3 times with 70 ml of MTB each time. After drying over Na₂SO₄, the solvent was removed in vacuo. Chromatography on silica gel with EA afforded 22.5 mg of a viscous oil.
$R_f$(EA/MeOH 5:1)=0.31 MS (ES⁺): 402 f) N-[4-(3,3-Dimethyl-1,1-dioxo-isothiazolidin-2-yl)-5-methanesulfonyl-2-methylbenzoyl]guanidine, hydrochloride 22.5 mg of N-[4-(3,3-dimethyl-1,1-dioxoisothiazolidin-2-yl)-5-methanesulfonyl-2-methylbenzoyl]guanidine were taken up in 5 ml of acetone, and 0.5 ml of a 4N aqueous HCl solution was added. The volatile constituents were removed in vacuo and then coevaporated 3 times with 5 ml of toluene each time. 23.9 mg of an amorphous solid were obtained.

Example 4

N-[4-(1,1-Dioxo-4-phenylisothiazolidin-2-yl)-5-methanesulfonyl-2-methylbenzoyl]guanidine, hydrochloride

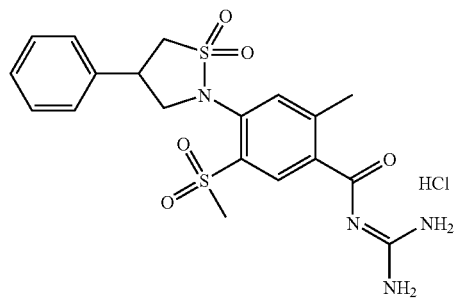

a) Methyl 4-(1,1-dioxo-4-phenylisothiazolidin-2-yl)-5-methanesulfonyl-2-methylbenzoate 600 mg of methyl 4-fluoro-5-methanesulfonyl-2-methylbenzoate (Journal of Medicinal Chemistry (1997), 40(13), 2017), 600 mg of 4-phenyl-isothiazolidine 1,1-dioxide (Pharmaceutical Chemistry Journal (Translation of Khimiko-Farmatsevticheskii Zhurnal) (2000), Volume Date 1999, 33(11), 598) and 2.379 g of Cs₂CO₃ were stirred in 20 ml of anhydrous DMF at RT for 4 hours. The reaction mixture was then poured into 220 ml of a half-saturated aqueous NaHCO₃ solution and extracted 3 times with 140 ml of EA each time. After drying over Na₂SO₄, the solvent was removed in vacuo. Chromatography on silica gel with DIP afforded 865 mg of a colorless oil.
$R_f$(DIP)=0.32 MS (DCI): 424 b) N-[4-(1,1-Dioxo-4-phenylisothiazolidin-2-yl)-5-methanesulfonyl-2-methyl-benzoyl]guanidine 860 mg of methyl 4-(1,1-dioxo-4-phenylisothiazolidin-2-yl)-5-methanesulfonyl-2-methylbenzoate were reacted in analogy to Example 1 b) to result in 737 mg of a colorless amorphous solid.
$R_f$(EA/MeOH 10:1)=0.54 MS (ES⁺): 450 c) N-[4-(1,1-Dioxo-4-phenylisothiazolidin-2-yl)-5-methanesulfonyl-2-methyl-benzoyl]guanidine, hydrochloride 737 mg of N-[4-(1,1-dioxo-4-phenylisothiazolidin-2-yl)-5-methanesulfonyl-2-methylbenzoyl]guanidine were dissolved in 20 ml of acetone, and 2 ml of a 2N aqueous HCl solution were added. The volatile constituents were then removed in vacuo. This was followed by coevaporation 3 times with 20 ml of toluene each time and finally drying under medium vacuum. 728 mg of white crystals were obtained, mp 259° C. (with decomposition).

Examples 5 and 6

N-[4-(1,1-Dioxo-4-phenylisothiazolidin-2-yl)-5-methanesulfonyl-2-methylbenzoyl]guanidine, hydrochloride and N-[4-(1,1-dioxo-4-phenylisothiazolidin-2-yl)-5-methanesulfonyl-2-methylbenzoyl]guanidine, hydrochloride

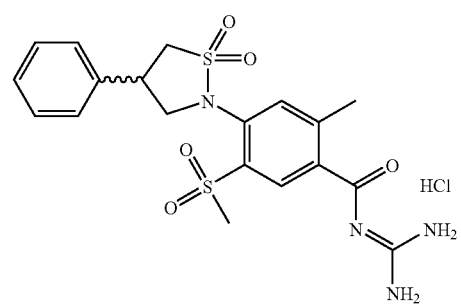

94 mg of N-[4-(1,1-dioxo-4-phenylisothiazolidin-2-yl)-5-methanesulfonyl-2-methylbenzoyl]guanidine, hydrochloride were chromatographed on Chiralpack AD/H 32 250×4.6 with HEP/EtOH/MeOH 1:1:1 to result in Examples 5 and 6:

Example 5

N-[4-(1,1-Dioxo-4-phenylisothiazolidin-2-yl)-5-methanesulfonyl-2-methylbenzoyl]guanidine, hydrochloride, enantiomer A: 22 mg of white crystals.

Retention time (Chiralpack AD/H 32 250×4.6 with HEP/EtOH/MeOH 1:1:1): 5.76 minutes

Example 6

N-[4-(1,1-Dioxo-4-phenylisothiazolidin-2-yl)-5-methanesulfonyl-2-methylbenzoyl]guanidine, hydrochloride, enantiomer B: 37 mg of white crystals Retention time (Chiralpack AD/H 32 250×4.6 with HEP/EtOH/MeOH 1:1:1): 13.05 minutes

Example 7

N-{4-[4-(4-Fluorophenyl)-1,1-dioxoisothiazolidin-2-yl]-5-methanesulfonyl-2-methylbenzoyl}guanidine, hydrochloride

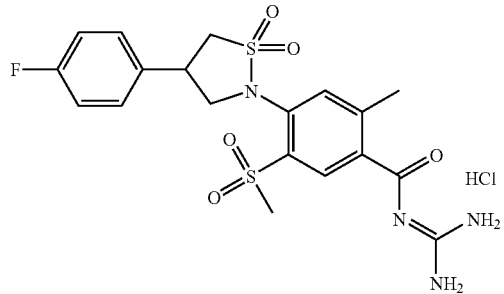

a) 2-(4-Fluorophenyl)ethenesulfonyl chloride 227 ml of $SO_2Cl_2$ were added dropwise to 257 ml of anhydrous DMF cooled to 3° C., during which the temperature rose to 33° C. Stirring at RT for 30 minutes was followed by dropwise addition of 223 ml of 1-fluoro-4-vinylbenzene, during which the temperature of the solution rose to 32° C. The reaction mixture was slowly warmed to a bath temperature of 60° C., with the internal temperature reaching 72° C. Stirring at 70° C. for 3 hours and 45 minutes was followed by pouring the reaction mixture in portions into 4 kg of ice. This was followed by extraction once with 1 l and 5 times with 800 ml of MTB each time. Drying over $Na_2SO_4$ and removal of the solvent in vacuo resulted in 163 g of a viscous oil, which was reacted without further purification.
$R_f$(EA/HEP 1:4)=0.49 b) Phenyl 2-(4-fluorophenyl)ethenesulfonate 163 g of 2-(4-fluorophenyl)ethenesulfonyl chloride were dissolved in 1.5 l of toluene and, at RT, 69.64 g of phenol were added. Subsequently, at RT, 103 ml of triethylamine were added dropwise, during which the temperature rose to 44° C. The mixture was then stirred at RT for 90 minutes, left to stand for 16 hours and stirred at RT for a further 2 hours. The solvent was then removed in vacuo, and the crude product was taken up in 2.5 l of EA. Washing 3 times with 750 ml of a saturated aqueous NaHCO3 solution was followed by washing 3 times with 750 ml of 2 N aqueous HCl solution each time. After drying over $Na_2SO_4$, the solvent was removed in vacuo. The product was then stirred in 350 ml of HEP for 1 hour and, on cooling, the product crystallized and was washed with HEP and dried under medium vacuum. 145.0 g of white crystals were obtained, mp 108° C.
$R_f$(EA/HEP 1:6)=0.26 MS (DCI): 279 c) Phenyl 2-(4-fluorophenyl)-2-nitroethanesulfonate 56.3 g of sodium methanolate were taken up in 1 l of DMSO and, at RT, 56.3 ml of nitromethane were added dropwise. The internal temperature rose to 40° C. during this. Then, at a temperature between 26° C. and 30° C., a solution of 145.0 g of phenyl 2-(4-fluorophenyl)ethenesulfonate in 1 l of DMSO was added dropwise. Stirring at RT for 1 hour was followed by leaving to stand at RT for 16 hours and then stirring at RT for a further 6 hours and 30 minutes. The reaction mixture was then poured into 8 kg of ice and extracted 5 times with 2 l of EA each time. After drying over $Na_2SO_4$, the solvent was removed in vacuo. Chromatography on silica gel with EA/HEP 1:5 afforded 77.35 g of a colorless oil.
$R_f$(EA/HEP 1:5)=0.19 d) Phenyl 3-amino-2-phenylpropane-1-sulfonate 71.00 g of phenyl 2-(4-fluorophenyl)-2-nitroethanesulfonate were dissolved in 200 ml of MeOH and 50 ml of THF, and 2 g of Raney nickel washed until neutral were added. Hydrogenation was carried out under a pressure of 5.5 bar of hydrogen at RT for 40 hours. The catalyst was then filtered off and the solvent was removed in vacuo. 61.01 g of an amorphous solid were obtained.
$R_f$(EA/MeOH 5:1)=0.38 MS (ES$^+$): 309 e) 4-(4-Fluorophenyl)isothiazolidine 1,1-dioxide 61.01 g of phenyl 3-amino-2-phenylpropane-1-sulfonate were dissolved in 800 ml of THF, and 80 ml of water and 22.23 g of KOH were added. Stirring at RT for 15 hours was followed by boiling under reflux for 5 hours. The solvent was then removed in vacuo, and the residue was taken up in 1 l of a saturated aqueous $NaHSO_4$ solution and extracted 3 times with 500 ml of EA each time. After drying over $MgSO_4$, the solvent was removed in vacuo. Chromatography on silica gel with DIP afforded 29.00 g of colorless crystals, mp 155° C.
$R_f$(DIP)=0.18 MS (DCI): 215 f) Methyl 4-[4-(4-fluorophenyl)-1,1-dioxoisothiazolidin-2-yl]-5-methanesulfonyl-2-methylbenzoate 18.00 g of 4-(4-fluorophenyl)isothiazolidine 1,1-dioxide, 20.59 g of methyl 4-fluoro-5-methanesulfonyl-2-methylbenzoate (Journal of Medicinal Chemistry (1997), 40(13), 2017) and 81.75 g of $Cs_2CO_3$ were stirred in 500 ml of anhydrous DMF at RT for 5 hours. Then a further 2.00 g of methyl 4-fluoro-5-methanesulfonyl-2-methylbenzoate were added, and the mixture was stirred at RT for 1 hour and left to stand at RT for 15 hours. The reaction mixture was poured into 1800 ml of water and stirred at RT for 1 hour, and the product was filtered off with suction. The product was then dissolved in 1 l of EA, and the solution was mixed with $MgSO_4$ and activated carbon and stirred at RT for 15 minutes. It was then filtered and the solvent was removed in vacuo. 35.00 g of a colorless foam were obtained.
$R_f$(DIP)=0.21 MS (ES$^-$): 441 g) N-{4-[4-(4-Fluorophenyl)-1,1-dioxoisothiazolidin-2-yl]-5-methanesulfonyl-2-methylbenzoyl}guanidine 44.48 g of KOtBu were dissolved in 800 ml of anhydrous DMF and, at RT, 45.44 g of guanidinium chloride were added. After stirring at RT for 1 hour, the solution was poured into a solution of 35.00 g of methyl 4-[4-(4-fluoro-phenyl)-1,1-dioxoisothiazolidin-2-yl]-5-methanesulfonyl-2-methylbenzoate in 300 ml of anhydrous DMF. The mixture was then stirred at RT for 5 hours. It was then poured into 2 l of water, adjusted to pH=8 with aqueous HCl solution and extracted 5 times with 300 ml of EA each time. After drying over MgSO$_4$, the solvent was removed in vacuo.

Recrystallization from EA resulted in 27.50 g of colorless crystals, mp 177-178° C.
R$_f$(EA/MeOH 10:1)=0.45 MS (ES$^+$): 468 h) N-{4-[4-(4-Fluorophenyl)-1,1-dioxoisothiazolidin-2-yl]-5-methanesulfonyl-2-methylbenzoyl}guanidine, hydrochloride 562 mg of N-{4-[4-(4-fluorophenyl)-1,1-dioxoisothiazolidin-2-yl]-5-methanesulfonyl-2-methylbenzoyl}guanidine were dissolved in 20 ml of acetone and 2 ml of a 4N aqueous HCl solution added. The volatile constituents were removed in vacuo, followed by coevaporation 3 times with 20 ml of toluene each time and finally drying under medium vacuum. 587 mg of white crystals were obtained, mp 250° C. (with decomposition).

Examples 8 and 9

N-{4-[4-(4-Fluorophenyl)-1,1-dioxoisothiazolidin-2-yl]-5-methanesulfonyl-2-methylbenzoyl}guanidine, hydrochloride and N-{4-[4-(4-fluorophenyl)-1,1-dioxoisothiazolidin-2-yl]-5-methanesulfonyl-2-methyl-benzoyl}guanidine, hydrochloride

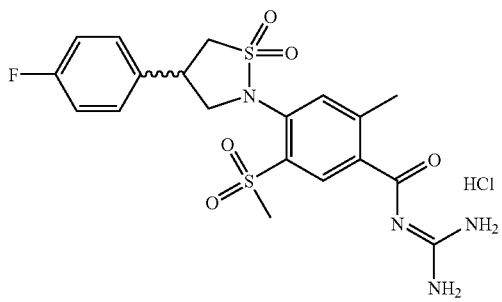

To separate the enantiomers of the title compound of Example 7, 27.50 g of the racemate 7 g) were chromatographed on a column which was packed with Chiralpack AD/10, 20 µM and had dimensions 400 mm×100 mm using HEP/EtOH/MeOH 2:1:1, 300 ml per minute, and reacted further to give Examples 8 and 9:

Example 8

N-{4-[4-(4-Fluorophenyl)-1,1-dioxoisothiazolidin-2-yl]-5-methanesulfonyl-2-methlbenzoyl}guanidine, hydrochloride, enantiomer A a) N-{4-[4-(4-Fluorophenyl)-1,1-dioxoisothiazolidin-2-yl]-5-methanesulfonyl-2-methylbenzoyl}guanidine enantiomer A, retention time of abovementioned system: 16.5 minutes 12.2 g of white crystals; [□]25° C. D=−49.3 b) N-{4-[4-(4-Fluorophenyl)-1,1-dioxoisothiazolidin-2-yl]-5-methanesulfonyl-2-methylbenzoyl}guanidine, hydrochloride, enantiomer A 84 mg of N-{4-[4-(4-fluorophenyl)-1,1-dioxoisothiazolidin-2-yl]-5-methanesulfonyl-2-methylbenzoyl}guanidine enantiomer A were converted into the hydrochloride in analogy to Example 7h), and 90 mg of white crystals were obtained.

Example 9

N-{4-[4-(4-Fluorophenyl)-1,1-dioxoisothiazolidin-2-yl]-5-methanesulfonyl-2-methylbenzoyl}guanidine, hydrochloride, enantiomer B a) N-{4-[4-(4-Fluorophenyl)-1,1-dioxoisothiazolidin-2-yl]-5-methanesulfonyl-2-methylbenzoyl}guanidine, enantiomer B, retention time of abovementioned system: 22.0 minutes 11.8 g of white crystals; [□]25° C. D=+49.4 b) N-{4-[4-(4-Fluorophenyl)-1,1-dioxoisothiazolidin-2-yl]-5-methanesulfonyl-2-methylbenzoyl}guanidine, hydrochloride, enantiomer B 5.00 g of N-{4-[4-(4-fluorophenyl)-1,1-dioxoisothiazolidin-2-yl]-5-methanesulfonyl-2-methylbenzoyl}guanidine enantiomer B were converted into the hydrochloride in analogy to Example 7h), and 5.32 g of white crystals were obtained.

Example 10

N-[4-(1,1-Dioxo-4-phenyl-1-[1,2]thiazinan-2-yl)-5-methanesulfonyl-2-methylbenzoyl]guanidine

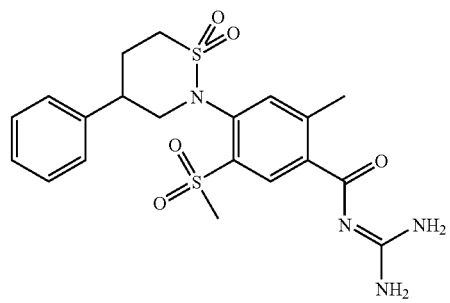

Example 10 was synthesized in analogy to Example 4 using 4-phenyl-[1,2]thiazinane 1,1-dioxide (J. Org. Chem. 1991, 56, 3549) as starting material.
R$_f$(EA/MeOH 5:1)=0.40 MS (ES$^+$): 464

Example 11

N-[4-(5-Cyclopropyl-1,1-dioxo-1-[1,2,5]thiadiazolidin-2-yl)-5-methanesulfonyl-2-methlbenzoyl]guanidine

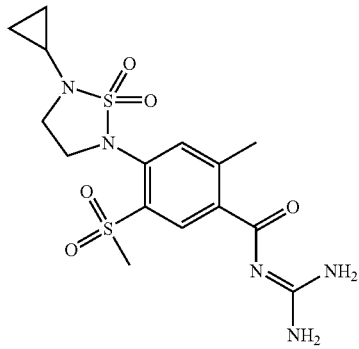

a) tert-butyl cyclopropylsulfamoylcarbamate

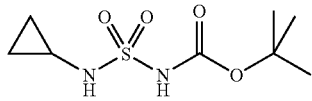

1.33 ml of t-BuOH were dissolved in 50 ml of anhydrous $CH_2Cl_2$ and, at RT, 2.00 g of chlorosulfonyl isocyanate were added dropwise. During this, the internal temperature rose to 30° C. Stirring at RT for 1 hour was followed by dropwise addition of 1.96 ml of cyclopropylamine and leaving the reaction mixture to stand at RT for 16 hours. It was then washed 3 times with 15 ml of water each time. After drying over $Na_2SO_4$, the solvent was removed in vacuo. 1.3 g of an amorphous solid were obtained.
MS (DCI): 237 b) tert-butyl 5-cyclopropyl-1,1-dioxo-[1,2,5]thiadiazolidine-2-carboxylate

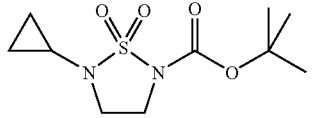

410 mg of tert-butyl cyclopropylsulfamoylcarbamate, 150 µl of 1,2-dibromoethane and 719 mg of $K_2CO_3$ were boiled under reflux in 6 ml of anhydrous acetone for 9 hours. The reaction mixture was left to stand at RT for 15 hours. Then 20 mg of tetrabutylammonium iodide were added, and the mixture was boiled under reflux for 9 hours. It was then diluted with 100 ml of EA and washed twice with 10 ml of water each time. After drying over $Na_2SO_4$, the solvent was removed in vacuo. 400 mg of a colorless oil were obtained.
MS (DCI): 263 c) 2-Cyclopropyl-[1,2,5]thiadiazolidine 1,1-dioxide

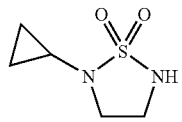

400 mg of tert-butyl 5-cyclopropyl-1,1-dioxo-[1,2,5]thiadiazolidine-2-carboxylate were dissolved in 10 ml of $CH_2Cl_2$/trifluoroacetic acid 1:1 and left to stand for 2 hours. The volatile constituents were removed in vacuo and coevaporated twice with 50 ml of $CH_2Cl_2$ each time. 410 mg of pale yellow oil were obtained and were directly employed further.

d) Methyl 4-(5-cyclopropyl-1,1-dioxo-[1,2,5]thiadiazolidin-2-yl)-5-methanesulfonyl-2-methylbenzoate

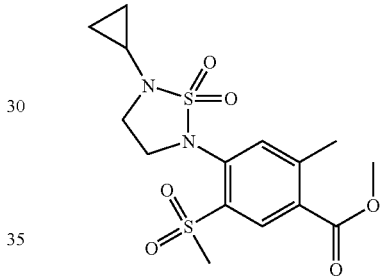

203 mg of 2-cyclopropyl-[1,2,5]thiadiazolidine 1,1-dioxide, 308 mg of methyl 4-fluoro-5-methanesulfonyl-2-methylbenzoate and 2.44 g of $Cs_2CO_3$ were stirred in 25 ml of anhydrous DMF at 80° C. for 5 hours. Standing at RT for 2 days was followed by dilution with 200 ml of EA and washing 3 times with 20 ml of water each time. After drying over $Na_2SO_4$, the solvent was removed in vacuo. Chromatography on silica gel with DIP afforded 230 mg of an amorphous solid.
$R_f$(DIP)=0.13 MS (DCI): 389 e) N-[4-(5-Cyclopropyl-1,1-dioxo-1-[1,2,5]thiadiazolidin-2-yl)-5-methanesulfonyl-2-methylbenzoyl]guanidine 191 mg of KOtBu were dissolved in 10 ml of anhydrous DMF and, at RT, 260 mg of guanidinium chloride were added. Stirring at RT for 30 minutes was followed by pouring the solution into 220 mg of methyl 4-(5-cyclopropyl-1,1-dioxo-[1,2,5]thiadiazolidin-2-yl)-5-methanesulfonyl-2-methylbenzoate. The mixture was then stirred at RT for 5 hours. It was then poured into 50 ml of water, adjusted to pH=8 with aqueous HCl solution and extracted 3 times with 30 ml of EA each time. After drying over $Na_2SO_4$, the solvent was removed in vacuo. Chromatography on silica gel with EA/MeOH 10:1 afforded 163 mg of an amorphous solid.
$R_f$(EA/MeOH 10:1)=0.28 MS (ES$^+$): 415

Example 12

N-[4-(6-Cyclopropyl-1,1-dioxo-1-[1,2,6]thiadiazinan-2-yl)-5-methanesulfonyl-2-methlbenzoyl]guanidine

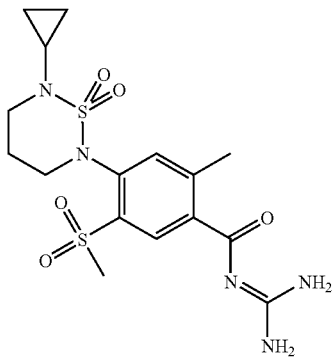

Example 12 was synthesized in analogy to Example 11.

$R_f$(EA/MeOH 10:1)=0.29 MS (ES$^+$): 429

Example 13

N-[4-(1,1-Dioxo-1-isothiazolidin-2-yl)-3-trifluoromethyl-benzoyl]guanidine

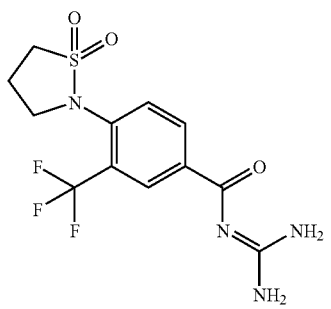

Example 13 was synthesized in analogy to Example 1 using methyl 4-fluoro-3-trifluoromethylbenzoate as starting material.

$R_f$(EA/MeOH 10:1)=0.53 MS (ES$^+$) 351 a) Methyl 4-fluoro-3-trifluoromethylbenzoate 5 g of 4-fluoro-3-trifluoromethylbenzoic acid and 9 ml SOCl$_2$ were stirred in 50 ml of MeOH at 60° C. for 8 h. The volatile constituents were then removed in vacuo to result in 5.1 g of a colorless oil, which was employed further without purification.

$R_f$(EA/MeOH 10:1)=0.74 MS (DCI) 223

Example 14

N-[4-(1,1-Dioxo-1-[1,2]thiazinan-2-yl)-3-trifluoromethyl-benzoyl]guanidine

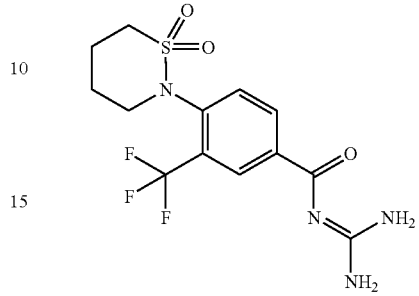

Example 14 was synthesized in analogy to Example 1 using methyl 4-fluoro-3-trifluoromethylbenzoate as starting material (methyl 4-fluoro-3-trifluoromethylbenzoate synthesized as in Example 13a))

$R_f$(EA/MeOH 10:1)=0.62

Determination of the NHE Inhibition

The inhibitory concentration IC$_{50}$ for NHE-1 inhibition was determined as follows:

IC$_{50}$ for NHE-1 inhibition was determined in an FLIPR assay by measurement of the pH$_i$ recovery in transfected cell lines which express human NHE-1.

The assay was carried out in an FLIPR (fluorometric imaging plate reader) with black-walled 96-well microtiter plates with clear bases. The transfected cell lines expressing the various NHE subtypes (the parental cell line LAP-1 shows no endogenous NHE activity as a result of mutagenesis and subsequent selection) were seeded the preceding day at a density of ~25 000 cells/well.

The growth medium for the transfected cells (Iscove+10% fetal calf serum) additionally contained G418 as selection antibiotic in order to ensure the presence of the transfected sequences.

The actual assay started with the removal of the growth medium and addition of 100 µl of loading buffer per well (5 µM BCECF-AM [2',7'-bis(carboxyethyl)-5- (and -6-)carboxyfluorescein, acetoxymethyl ester] in 20 mM NH$_4$Cl, 115 mM choline chloride, 1 mM MgCl$_2$, 1 mM CaCl$_2$, 5 mM KCl, 20 mM HEPES, 5 mM glucose; pH 7.4 [adjusted with KOH]). The cells were then incubated at 37° C. for 20 minutes. This incubation led to loading of the cells with the fluorescent dye whose fluorescence intensity depends on pHi, and with NH$_4$Cl which made the cells slightly alkaline.

The nonfluorescent dye precursor BCECF-AM is, as ester, membrane-permeable. The actual dye BCECF is not membrane-permeable but is liberated inside cells by esterases.

After this incubation for 20 minutes, the loading buffer which contained NH$_4$Cl and free BCECF-AM was removed by washing three times in a cell washer (Tecan Columbus) with in each case 400 µl of washing buffer (133.8 mM choline chloride, 4.7 mM KCl, 1.25 mM MgCl$_2$, 1.25 mM CaCl$_2$, 0.97 mM K$_2$HPO$_4$, 0.23 mM KH$_2$PO$_4$, 5 mM HEPES, 5 mM glucose pH 7.4 [adjusted with KOH]). The residual volume which remained in the wells was 90 µl (50-125 µl possible). This washing step removed the free BCECF-AM and resulted, as a consequence of the removal of the external NH$_4{}^+$ ions, in intracellular acidification (~pH$_i$ 6.3-6.4).

Since the equilibrium of intracellular $NH_4^+$ with $NH_3$ and $H^+$ was disturbed by the removal of the extracellular $NH_4^+$ and by the subsequent instantaneous passage of the $NH_3$ through the cell membrane, the washing process resulted in $H^+$ remaining inside the cells, which was the cause of the intracellular acidification. This may eventually lead to cell death if it persists long enough.

It was important at this point that the washing buffer was sodium-free (<1 mM) because extracellular sodium ions would lead to an instantaneous recovery of the $pH_i$ through the activity of the cloned NHE isoforms. It was likewise important for all the buffers used (loading buffer, washing buffer, recovery buffer) not to contain any $HCO_3^-$ ions, because the presence of bicarbonate would lead to activation of interfering bicarbonate-dependent $pH_i$ regulatory systems present in the parental LAP-1 cell line.

The microtiter plates with the acidified cells were then (up to 20 minutes after the acidification) transferred to the FLIPR. In the FLIPR, the intracellular fluorescent dye was excited by light with a wavelength of 488 nm generated by an argon laser, and the measured parameters (laser power, illumination time and aperture of the CCD camera incorporated in the FLIPR) were chosen so that the average fluorescence signal per well was between 30 000 and 35 000 relative fluorescence units.

The actual measurement in the FLIPR started with a photograph being taken by the CCD camera every two seconds under software control. After ten seconds, the recovery of the intracellular pH was initiated by adding 90 µl of recovery buffer (133.8 mM NaCl, 4.7 mM KCl, 1.25 mM $MgCl_2$, 1.25 mM $CaCl_2$, 0.97 mM $K_2HPO_4$, 0.23 mM $KH_2PO_4$, 10 mM HEPES, 5 mM glucose; pH 7.4 [adjusted with NaOH]) by means of the 96-well pipettor incorporated in the FLIPR.

Positive control wells (100% NHE activity) were those to which pure recovery buffer is added, while negative controls (0% NHE activity) received washing buffer. Recovery buffer with twice the concentration of test substance was added to all the other wells. Measurement in the FLIPR terminated after 60 measurements (two minutes).

The raw data are exported into the ActivityBase program. This program firstly calculates the NHE activities for each tested substance concentration and, from these, the $IC_{50}$ values for the substances. Since the progress of $pH_i$ recovery was not linear throughout the experiment, but fell at the end owing to decreasing NHE activity at higher $pH_i$ values, it was important to select for evaluation of the measurement the part in which the increase in fluorescence of the positive controls was linear.

| Example | NHE1 inhibition $IC_{50}$ [nM] |
|---|---|
| 1 | 38 |
| 2 | 144 |
| 3 | 195 |
| 4 | 6 |
| 5 | 13 |
| 6 | 45 |
| 7 | 19 |
| 8 | 12 |
| 9 | 23 |
| 10 | 51 |
| 11 | 113 |
| 12 | 1522 |
| 13 | 20 |
| 14 | 13 |

In vivo pharmacokinetics—profiling with the "n in one method"

The exposure data and the half-life were determined as characteristic pharmacokinetic data as follows:

The NHE-1 inhibitor of Example 9 of the invention and, as reference substance, the known NHE-1 inhibitor cariporide with the formula

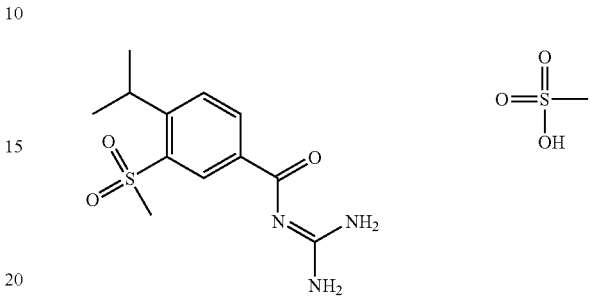

were dissolved in an aqueous, slightly acidic medium (water, pH 4, adjusted with 1M hydrochloric acid). The concentration of the aqueous formulation prepared in this way was about 1.5 mg of each substance per 1 g of solution. 10 ml of this formulation were administered as a single bolus by catheter into the jugular vein of a fasting male beagle dog (dose about 1 mg of each substance administered per kg of the dog's body weight). Blood samples were taken by means of a second catheter after 5 min, 15 min, 30 min, 1 h, 2 h, 4 h, 8 h and 24 h, and heparinized plasma was prepared by centrifugation at 1000 G in appropriate plasma tubes.

The plasma samples were worked up and, after an HPLC separation, quantified by MS/MS. The high specificity of this method permitted simultaneous determination of a plurality of substances. The exposures could be calculated using the WinNonlin computer program from the concentration-time plots (see FIG. 1) and compared with the exposure of the known NHE-1 reference substance. Since the various substances were measured in the same animal at the same time, the result was an accurate comparison of the compounds, and a ranking of the volumes of distribution was possible.

| Compound | Half-life [h] |
|---|---|
| Example 9 | 4.6 |
| Reference substance cariporide | 3.3 |

It is clearly evident from the concentration-time plots in FIG. 1 that the compound of the invention show a distinctly greater exposure than the reference substance cariporide.

The captions and signs in the figure were as follows:

FIG. 1: concentration-time plots in the blood plasma of dogs after administration of in each case approx. 1 mg/kg of the compound of Example 9 and of cariporide.

y axis: concentration of the measured compound in the pg/ml in plasma x axis: time in h

The invention claimed is:
1. A compound of the formula I:

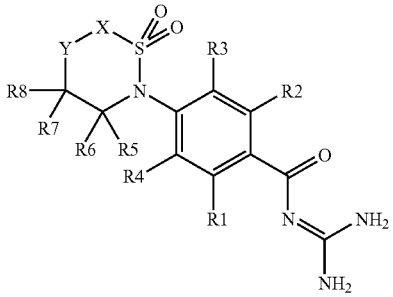

wherein:
R1 is hydrogen, alkyl having 1, 2, 3 or 4 carbon atoms, alkoxy having 1, 2, 3 or 4 carbon atoms, F, Cl, Br, I, —CN, NR13R14, —O—$(CH_2)_n$—$(CF_2)_o$—$CF_3$ or —$(SO_m)_q$—$(CH_2)_r(CF_2)_s$—$CF_3$;
   R13 and R14 are independently of one another hydrogen, alkyl having 1, 2, 3 or 4 carbon atoms or —$CH_2$—$CF_3$;
   m is zero, 1 or 2
   n, o, q, r and s are independently of one another zero or 1;
R2 is hydrogen, alkyl having 1, 2, 3 or 4 carbon atoms, alkoxy having 1, 2, 3 or 4 carbon atoms, F, Cl, Br, I, —CN, NR15R16,
   —O—$(CH_2)_u$—$(CF_2)_v$—$CF_3$ or —$(SO_w)_x$—$(CH_2)_y$—$(CF_2)_z$—$CF_3$;
   R15 and R16 are independently of one another hydrogen, alkyl having 1, 2, 3 or 4 carbon atoms or —$CH_2$—$CF_3$;
   w is zero, 1 or 2
   u, v, x, y and z are independently of one another zero or 1;
R3 is hydrogen, F, Cl, Br, I, —ON, —$SO_2CH_3$, alkoxy having 1, 2, 3 or 4 carbon atoms, NR9R10, —O—$(CH_2)_b$—$(CF_2)_c$—$CF_3$,
   —$(SO_d)_e$—$(CH_2)_f$—$(CF_2)_g$—$CF_3$, alkyl having 1, 2, 3, 4, 5 or 6 carbon atoms or cycloalkyl having 3, 4, 5, 6, 7 or 8 carbon atoms, in which 1, 2, 3 or 4 hydrogen atoms may be replaced by fluorine atoms;
   R9 and R10 are independently of one another hydrogen, alkyl having 1, 2, 3 or 4 carbon atoms or —$CH_2$—$CF_3$;
   b, c, e and g are independently of one another zero or 1;
   d is zero, 1 or 2;
   f is zero, 1, 2, 3 or 4;
or
R3 is —$(CH_2)_h$-phenyl or —O-phenyl,
   in which the phenyl radicals are unsubstituted or are substituted by 1, 2 or 3 radicals selected from the group consisting of series F, Cl, Br, I, —$O_j$—$(CH_2)_k$—$CF_3$, alkoxy having 1, 2, 3 or 4 carbon atoms, alkyl having 1, 2, 3 or 4 carbon atoms and —$SO_2CH_3$;
   j is zero or 1;
   k is zero, 1, 2 or 3;
   h is zero, 1, 2, 3 or 4;
or
R3 —$(CH_2)_{aa}$-heteroaryl,
   which is unsubstituted or is substituted by 1, 2 or 3 radicals selected from the group consisting of F, Cl, Br, I, —$O_{bb}$—$(CH_2)_{cc}$—$CF_3$, alkoxy having 1, 2, 3 or 4 carbon atoms, alkyl having 1, 2, 3 or 4 carbon atoms and —$SO_2CH_3$;
   bb is zero or 1;
   cc is zero or 1, 2 or 3;
   aa is zero, 1, 2, 3 or 4;
R4 is hydrogen, F, Cl, Br, I, —CN, —$SO_2CH_3$, alkoxy having 1, 2, 3 or 4 carbon atoms, NR11R12, —O—$(CH_2)_{ee}$—$(CF_2)_{ff}$—$CF_3$; —$(SO_{gg})_{hh}$—$(CH_2)_{jj}$—$(CF_2)_{kk}$—$CF_3$, alkyl having 1, 2, 3, 4, 5 or 6 carbon atoms or cycloalkyl having 3, 4, 5, 6, 7 or 8 carbon atoms, in which 1, 2, 3 or 4 hydrogen atoms may be substituted by fluorine atoms;
   R11 and R12 are independently of one another hydrogen, alkyl having 1, 2, 3 or 4 carbon atoms or —$CH_2$—$CF_3$;
   ee, ff, hh and kk are independently of one another zero or 1;
   gg is zero, 1 or 2;
   jj is zero, 1, 2, 3 or 4;
or
R4 is —$(CH_2)_{ll}$-phenyl or —O-phenyl,
   in which the phenyl radicals are unsubstituted or are substituted by 1, 2 or 3 radicals selected from the group consisting of F, Cl, Br, I, —$O_{mm}$—$(CH_2)_{nn}$—$CF_3$, alkoxy having 1, 2, 3 or 4 carbon atoms, alkyl having 1, 2, 3 or 4 carbon atoms and —$SO_2CH_3$;
   mm is zero or 1;
   nn is zero, 1, 2 or 3;
   ll zero, 1, 2, 3 or 4;
or
R4 is —$(CH_2)_{oo}$-heteroaryl,
   which is unsubstituted or is substituted by 1, 2 or 3 radicals selected from the group consisting of F, Cl, Br, I, —$O_{pp}$—$(CH_2)_{rr}$—$CF_3$, alkoxy having 1, 2, 3 or 4 carbon atoms, alkyl having 1, 2, 3 or 4 carbon atoms and —$SO_2CH_3$;
   pp is zero or 1;
   rr is zero, 1, 2 or 3;
   oo is zero, 1, 2, 3 or 4;
R5 and R6 are independently of one another hydrogen or alkyl having 1, 2, 3 or 4 carbon atoms;
R7 and R8 are independently of one another hydrogen, alkyl having 1, 2, 3 or 4 carbon atoms, cycloalkyl having 3, 4, 5, 6, 7 or 8 carbon atoms, —$CF_3$ or phenyl, where the phenyl radical is unsubstituted or is substituted by 1, 2 or 3 radicals selected from the group consisting of series F, Cl, Br, I, —$O_{ss}$—$(CH_2)_{tt}$—$CF_3$, alkoxy having 1, 2, 3 or 4 carbon atoms, alkyl having 1, 2, 3 or 4 carbon atoms and —$SO_2CH_3$;
   ss is zero or 1
   tt is zero, 1, 2 or 3;
   X is —$CH_2$
   uu is zero or 1;
   vv is zero, 1, 2 or 3;
   Y is a bond;
and the pharmaceutically acceptable salts thereof.
2. A compound according to claim 1, in which:
   R1 is hydrogen, alkyl having 1, 2, 3 or 4 carbon atoms, alkoxy having 1, 2, 3 or 4 carbon atoms, F, Cl, NR13R14, —O—$(CH_2)_n$—$(CF_2)_o$—$CF_3$ or —$(SO_m)_q$—$(CH_2)_r$—$(CF_2)_s$—$CF_3$;
   R13 and R14 are independently of one another hydrogen, methyl, ethyl or $CH_2$—$CF_3$;
   m is zero, 1 or 2
   n, o, q, r and s are independently of one another zero or 1;
   R2 is hydrogen, methyl, methoxy, F, Cl, —O—$CF_3$, —O—$CH_2$—$CF_3$ or —S—$CF_3$;
   R3 is hydrogen, F, Cl, —CN, —$SO_2CH_3$, methoxy, ethoxy, NR9R10, —O—$CF_3$,
   —O—$CH_2$—$CF_3$, —$SO_2CF_3$, —S—$CF_3$, —$CF_3$, alkyl having 1, 2, 3 or 4 carbon atoms or cycloalkyl having 3, 4, 5 or 6 carbon atoms, in which 1, 2, 3 or 4 hydrogen atoms may be substituted by fluorine atoms;

R9 and R10 are independently of one another hydrogen, methyl, ethyl or —CH$_2$—CF$_3$;

or

R3 is phenyl or —O-phenyl,
   in which the phenyl radicals are unsubstituted or are substituted by 1, 2 or 3 radicals selected from the group consisting of series F, Cl, —O—CF$_3$, —O—CH$_2$—CF$_3$, —S—CF$_3$, methoxy, ethoxy, alkyl having 1, 2, 3 or 4 carbon atoms and —SO$_2$CH$_3$;

R4 is hydrogen, F, Cl, —CN, —SO$_2$CH$_3$ or methyl;

R5 and R6 are independently of one another hydrogen, methyl or ethyl;

R7 and R8 are independently of one another hydrogen, alkyl having 1, 2, 3 or 4 carbon atoms, cycloalkyl having 3, 4, 5 or 6 carbon atoms, —CF$_3$ or phenyl, where the phenyl radical is unsubstituted or is substituted by 1, 2 or 3 radicals selected from the group consisting of series F, Cl, —O—CF$_3$, —O—CH$_2$—CF$_3$, —S—CF$_3$, methoxy, ethoxy, alkyl having 1, 2, 3 or 4 carbon atoms and —SO$_2$CH$_3$;

X is —CH$_2$

Y is a bond;

and the pharmaceutically acceptable salts thereof.

3. A compound according to claim 2, in which:

R1 is hydrogen, methyl, ethyl, methoxy, ethoxy, F, Cl, —O—CF$_3$, —O—CH$_2$—CF$_3$ or —S—CF$_3$;

R2 is hydrogen, F, Cl, —O—CF$_3$, —O—CH$_2$—CF$_3$ or —S—CF$_3$;

R3 is F, Cl, —CN, —SO$_2$CH$_3$, —CF$_3$, —O—CF$_3$, —O—CH$_2$—CF$_3$, —SO$_2$CF$_3$, —S—CF$_3$, alkyl having 1, 2, 3 or 4 carbon atoms or cycloalkyl having 3, 4, 5 or 6 carbon atoms, in which 1, 2, 3 or 4 hydrogen atoms may be replaced by fluorine atoms;

or

R3 is phenyl or —O-phenyl,
   in which the phenyl radicals are unsubstituted or are substituted by 1 or 2 radicals selected from the group consisting of series F, Cl, —O—CF$_3$, —O—CH$_2$—CF$_3$, —S—CF$_3$, methoxy, ethoxy, alkyl having 1, 2, 3 or 4 carbon atoms and —SO$_2$CH$_3$;

R4 is hydrogen or F;

R5 and R6 are independently of one another hydrogen or methyl;

R7 and R8 are independently of one another hydrogen, alkyl having 1, 2, 3 or 4 carbon atoms, cycloalkyl having 3, 4, 5 or 6 carbon atoms, —CF$_3$ or phenyl, where the phenyl radical is unsubstituted or is substituted by 1 or 2 radicals selected from the group consisting of series F, Cl, —O—CF$_3$, —O—CH$_2$—CF$_3$, —S—CF$_3$, methoxy, ethoxy, alkyl having 1, 2, 3 or 4 carbon atoms and —SO$_2$CH$_3$;

X is —CH$_2$

Y is a bond;

and the pharmaceutically acceptable salts thereof.

4. A compound according to claim 3, in which:

R1 is hydrogen, methyl, —O—CH$_2$—CF$_3$ or —S—CF$_3$;

R2 is hydrogen;

R3 is —CN, —SO$_2$CH$_3$, —CF$_3$, —O—CF$_3$, —O—CH$_2$—CF$_3$, —SO$_2$CF$_3$, —S—CF$_3$;

R4 is hydrogen;

R5 and R6 are hydrogen;

R7 is hydrogen;

R8 is alkyl having 1, 2, 3 or 4 carbon atoms, cycloalkyl having 3, 4, 5 or 6 carbon atoms, CF$_3$ or phenyl, where the phenyl radical is unsubstituted or is substituted by 1 or 2 radicals selected from the group consisting of series F, Cl, —O—CF$_3$, —O—CH$_2$—CF$_3$, —S—CF$_3$, methoxy, ethoxy, alkyl having 1, 2, 3 or 4 carbon atoms and —SO$_2$CH$_3$;

X is —CH$_2$

Y is a bond;

and the pharmaceutically acceptable salts thereof.

5. A compound according to claim 4, in which:

R1 is hydrogen, methyl, —O—CH$_2$—CF$_3$ or —S—CF$_3$;

R2 is hydrogen;

R3 is —CN, —SO$_2$CH$_3$, —CF$_3$, —O—CF$_3$, —O—CH$_2$—CF$_3$, —SO$_2$CF$_3$, —S—CF$_3$;

R4 is hydrogen;

R5 and R6 are independently of one another hydrogen or methyl;

R7 is hydrogen;

R8 is hydrogen;

X is —CH$_2$

Y is a bond;

and the pharmaceutically acceptable salts thereof.

6. A compound according to claim 5 selected from a group consisting of:
   N-[4-(1,1-dioxoisothiazolidin-2-yl)-5-methanesulfonyl-2-methylbenzoyl]guanidine,
   N-[4-(3,3-dimethyl-1,1-dioxoisothiazolidin-2-yl)-5-methanesulfonyl-2-methylbenzoyl]guanidine,
   N-[4-(1,1-dioxo-4-phenylisothiazolidin-2-yl)-5-methanesulfonyl-2-methylbenzoyl]guanidine,
   N-{4-[4-(4-fluorophenyl)-1,1-dioxoisothiazolidin-2-yl]-5-methanesulfonyl-2-methylbenzoyl}guanidine,
   N-[4-(5-cyclopropyl-1,1-dioxo-1-[1,2,5]thiadiazolidin-2-yl)-5-methanesulfonyl-2-methylbenzoyl]guanidine, and
   N-[4-(1,1-dioxo-1-isothiazolidin-2-yl)-3-trifluoromethylbenzoyl]guanidine,
   and pharmaceutically acceptable salts thereof.

7. A pharmaceutical composition comprising a compound of formula I according to claim 1 and a pharmaceutically acceptable carrier.

* * * * *